(12) United States Patent
Rosenbluth et al.

(10) Patent No.: US 7,691,121 B2
(45) Date of Patent: Apr. 6, 2010

(54) EMBOLECTOMY CATHETERS AND METHODS FOR TREATING STROKE AND OTHER SMALL VESSEL THROMBOEMBOLIC DISORDERS

(75) Inventors: Robert F. Rosenbluth, Laguna Niguel, CA (US); George R. Green, Jr., Costa Mesa, CA (US); Brian J. Cox, Laguna Niguel, CA (US); Thomas R. Sternweiler, Laguna Niguel, CA (US); Sean L. Chow, Tustin, CA (US); Richard R. Monetti, San Clemente, CA (US)

(73) Assignee: MicroVention, Inc., Tustin, CA (US)

( * ) Notice: Subject to any disclaimer, the term of this patent is extended or adjusted under 35 U.S.C. 154(b) by 0 days.

(21) Appl. No.: 10/730,860

(22) Filed: Dec. 9, 2003

(65) Prior Publication Data

US 2004/0133232 A1 Jul. 8, 2004

Related U.S. Application Data

(63) Continuation of application No. 09/437,530, filed on Nov. 10, 1999, now Pat. No. 6,685,722, which is a continuation-in-part of application No. 09/071,561, filed on May 1, 1998, now Pat. No. 6,511,492.

(51) Int. Cl.
*A61M 29/00* (2006.01)
(52) U.S. Cl. ............... 606/200; 604/96.01; 604/523
(58) Field of Classification Search ............... 606/1, 606/108, 159, 191–200, 213, 110, 113, 127, 606/128, 114; 604/96.01, 523
See application file for complete search history.

(56) References Cited

U.S. PATENT DOCUMENTS 3,568,659 A * 3/1971 Karnegis .................. 604/264

(Continued)

FOREIGN PATENT DOCUMENTS

EP 0 818 180 A 1/1998

(Continued)

OTHER PUBLICATIONS

Baxter Healthcare Corporation, Vascular Systems Division, a Fogarty Catheter with a new twist.

(Continued)

*Primary Examiner*—Michael J Milano
*Assistant Examiner*—Victor X Nguyen
(74) *Attorney, Agent, or Firm*—Inskeep IP Group, Inc.

(57) ABSTRACT

Embolectomy catheters, rapid exchange microcatheters, systems and methods for removing clots or other obstructive matter (e.g., thrombus, thromboemboli, embolic fragments of atherosclerotic plaque, foreign objects, etc.) from blood vessels. This invention is particularly useable for percutaneous removal of thromboemboli or other obstructive matter from small blood vessels of the brain, during an evolving stroke or period of cerebral ischemia. In some embodiments, the embolectomy catheters of this invention are advanceable with or over a guidewire which has been pre-inserted through or around the clot. Also, in some embodiments, the embolectomy catheters include clot removal devices which are deployable from the catheter after the catheter has been advanced at least partially through the clot. The clot removal device may included a deployable wire nest that is designed to prevent a blood clot from passing therethrough. The delivery catheter may include telescoping inner and outer tubes, with the clot removal device being radially constrained by the outer tube. Retraction of the outer tube removes the constraint on the clot removal device and permits it to expand to its deployed configuration. An infusion guidewire is particularly useful in conjunction with the embolectomy catheter, and permits infusion of medicaments or visualization fluids distal to the clot.

8 Claims, 29 Drawing Sheets

U.S. PATENT DOCUMENTS

| | | | | |
|---|---|---|---|---|
| 3,635,223 | A | 1/1972 | Klieman | |
| 3,923,065 | A | 12/1975 | Nozick et al. | |
| 3,996,938 | A | 12/1976 | Clark, III | |
| 4,030,503 | A | 6/1977 | Clark, III | |
| 4,046,150 | A | 9/1977 | Schwartz et al. | |
| 4,347,846 | A | 9/1982 | Dormia | |
| 4,425,908 | A | 1/1984 | Simon | |
| 4,590,938 | A | 5/1986 | Segura et al. | |
| 4,643,184 | A | 2/1987 | Mobin-Uddin | |
| 4,706,671 | A | 11/1987 | Weinrib | |
| 4,790,812 | A | 12/1988 | Hawkins | |
| 4,807,626 | A | 2/1989 | McGirr | |
| 4,873,978 | A | 10/1989 | Ginsburg | |
| 5,011,488 | A | 4/1991 | Ginsburg | |
| 5,034,001 | A * | 7/1991 | Garrison et al. | 606/198 |
| 5,057,114 | A | 10/1991 | Wittich et al. | |
| 5,059,178 | A | 10/1991 | Ya | |
| 5,092,839 | A | 3/1992 | Kipperman | |
| 5,167,239 | A * | 12/1992 | Cohen et al. | 600/585 |
| 5,488,960 | A * | 2/1996 | Toner | 604/264 |
| 5,527,326 | A | 6/1996 | Hermann et al. | |
| 5,540,707 | A * | 7/1996 | Ressemann et al. | 606/159 |
| 5,649,953 | A * | 7/1997 | Lefebvre | 606/200 |
| 5,814,064 | A * | 9/1998 | Daniel et al. | 606/159 |
| 5,882,329 | A * | 3/1999 | Patterson et al. | 604/500 |
| 5,895,398 | A | 4/1999 | Wensel et al. | |
| 5,895,411 | A | 4/1999 | Irie | |
| 5,908,435 | A * | 6/1999 | Samuels | 606/200 |
| 5,911,734 | A * | 6/1999 | Tsugita et al. | 606/200 |
| 5,941,869 | A * | 8/1999 | Patterson et al. | 604/508 |
| 5,941,896 | A * | 8/1999 | Kerr | 606/200 |
| 5,961,526 | A | 10/1999 | Chu | |
| 6,066,158 | A | 5/2000 | Engelson | |
| 6,319,242 | B1 * | 11/2001 | Patterson et al. | 604/508 |
| 6,511,492 | B1 * | 1/2003 | Rosenbluth et al. | 606/159 |
| 6,572,612 | B2 * | 6/2003 | Stewart et al. | 606/41 |
| 6,663,650 | B2 | 12/2003 | Sepetka et al. | |
| 6,685,722 | B1 * | 2/2004 | Rosenbluth et al. | 606/200 |
| 2003/0139764 | A1 * | 7/2003 | Levinson et al. | 606/200 |
| 2004/0236368 | A1 * | 11/2004 | McGuckin et al. | 606/200 |
| 2005/0038468 | A1 * | 2/2005 | Panetta et al. | 606/200 |
| 2005/0216051 | A1 * | 9/2005 | Mazzocchi et al. | 606/200 |

FOREIGN PATENT DOCUMENTS

| | | |
|---|---|---|
| WO | WO 97/38631 | 10/1997 |
| WO | WO 9920189 | 4/1999 |
| WO | WO 9923952 | 5/1999 |
| WO | WO 99/56801 | 11/1999 |

OTHER PUBLICATIONS

Broderick JP, Dept. of Neurology, University of Cincinnati Medical Center, Ohio, USA, Recanalization therapie for actue ischemic stroke, Aug. 4, 1999, http://www.ncbi.nlm.nih.gov/htbin-p...uery?uid=9932618....

Hill B, Fogarty TJ, Department of Surgery, Stanford University School of Medicine, CA, USA, The use of the Fogarty catheter in 1998, Aug. 4, 1999, http://www.ncbi.nlm.nih.gov/htbin-p...ery?uid=10386742....

Parsons RE et al., Department of Surgery, Montefiore Medical Center, University Hospital, Albert Einstein College of Medicine, New York, NY, USA, Fluoroscopically assisted thromboembolectomy: an improvd method for treating acute arterial occlusions, Aug. 4, 1999, http://www.ncbi.nlm.nih.gov/htbin-p...uery?uid=8792986....

* cited by examiner

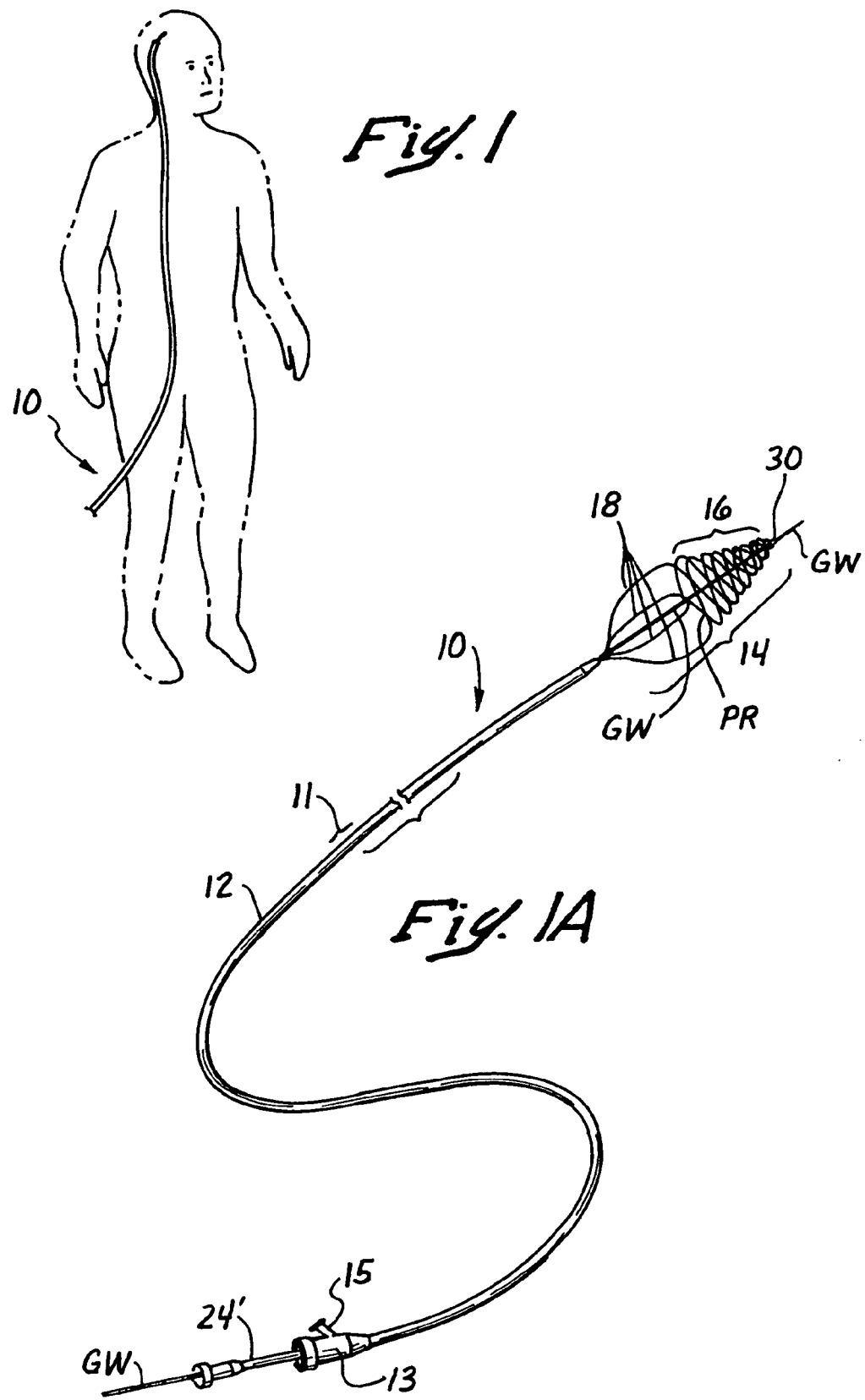

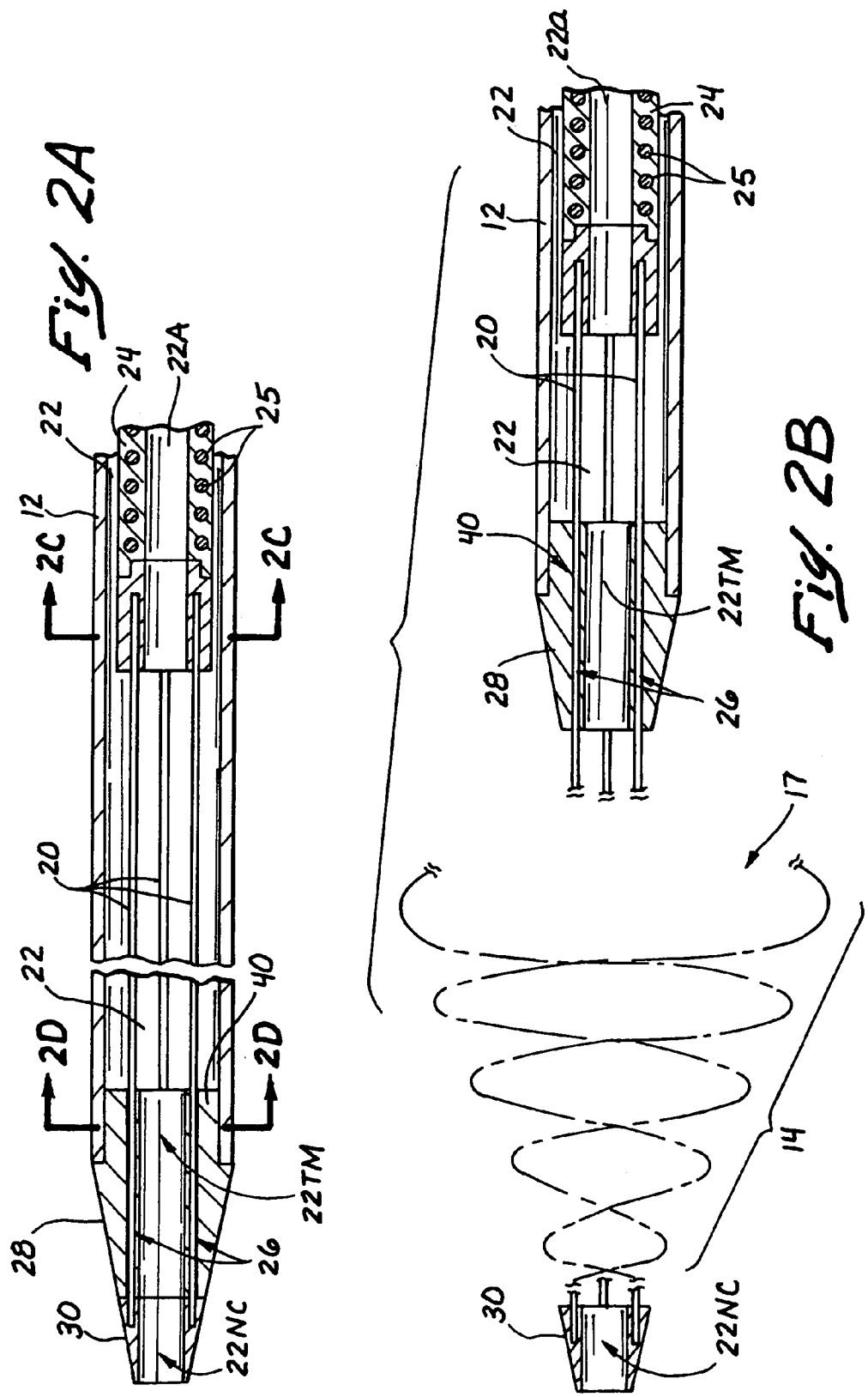

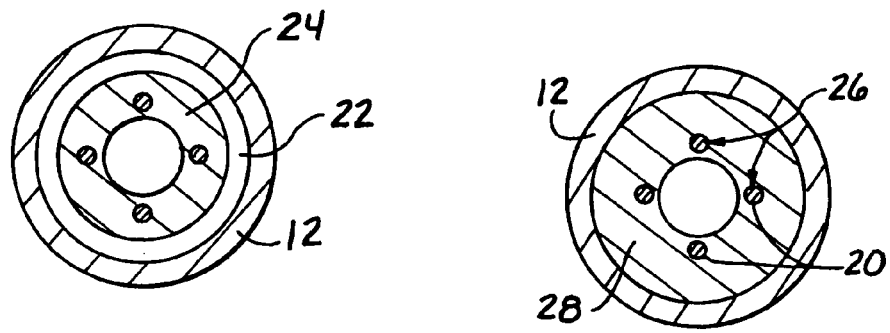
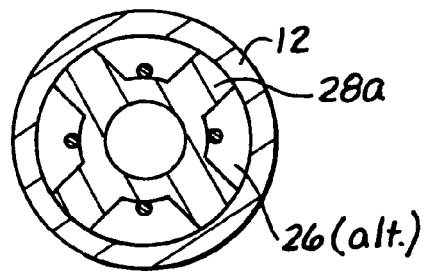
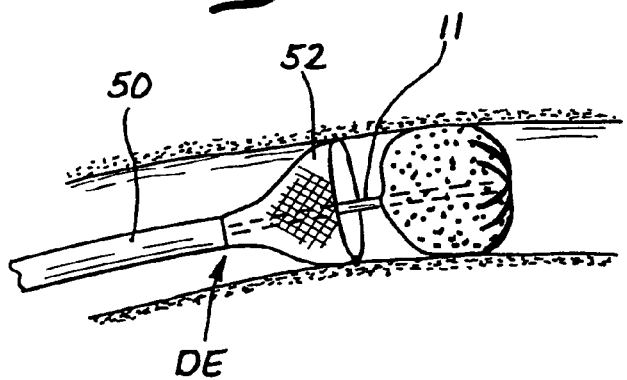

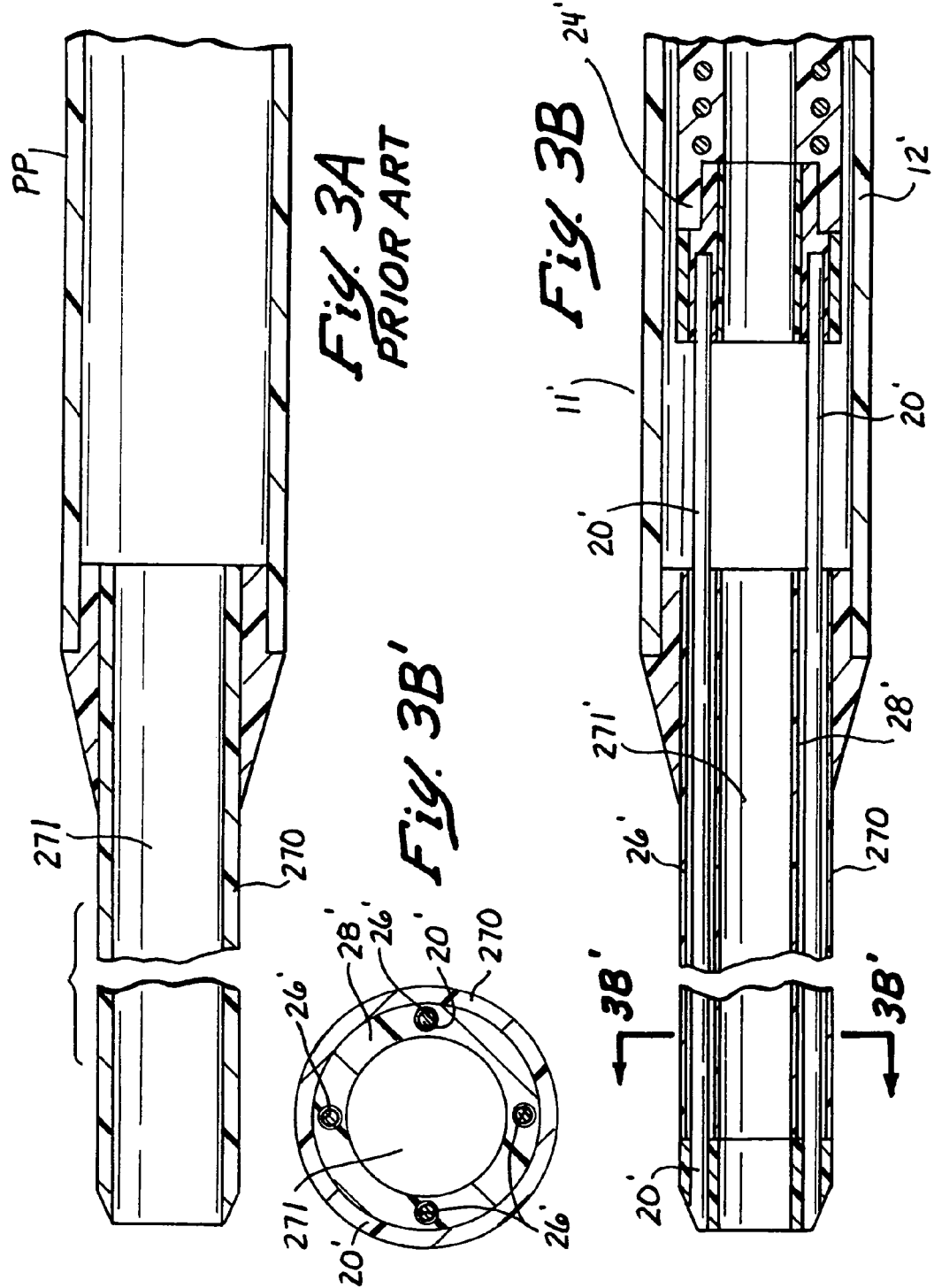

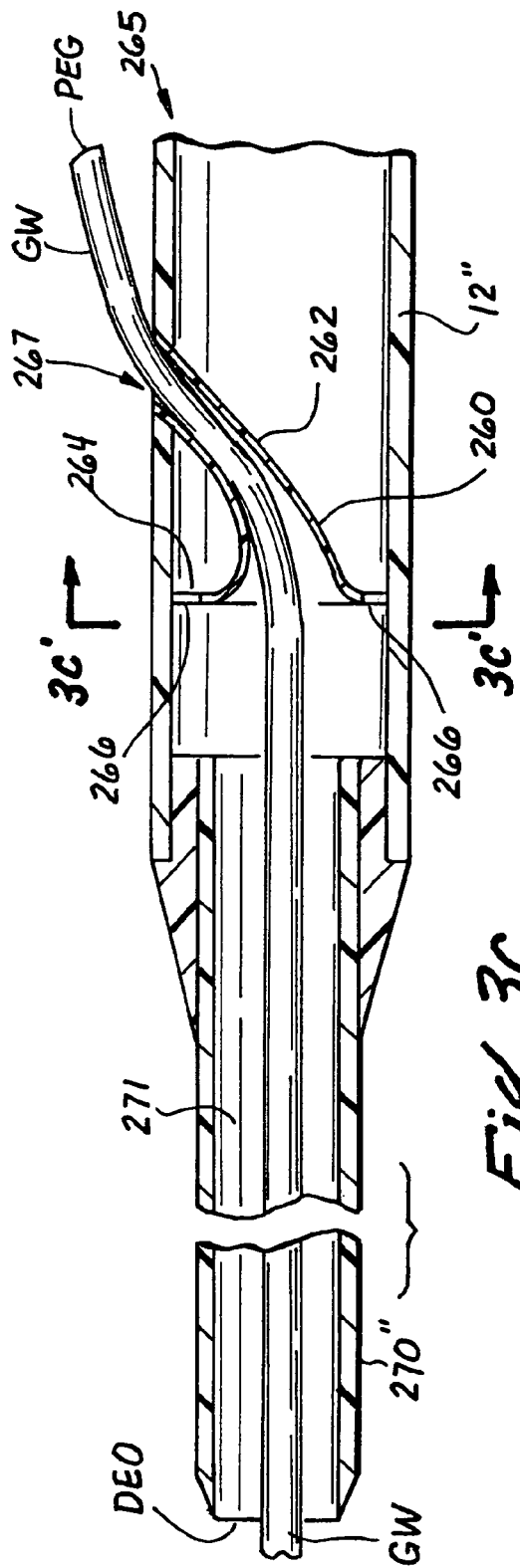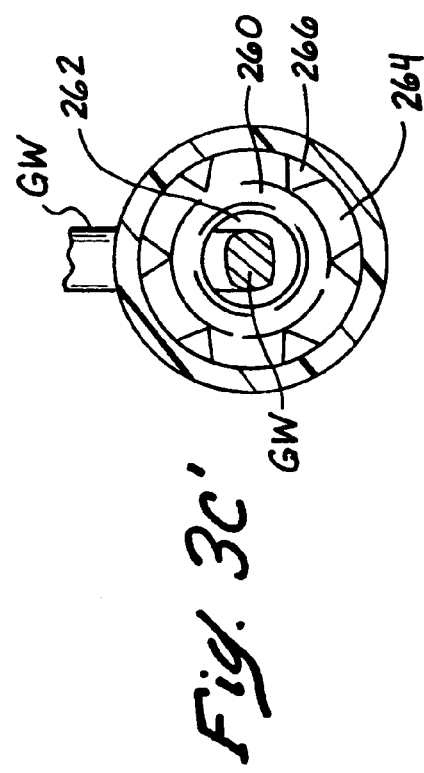
Fig. 3c
Fig. 3c'

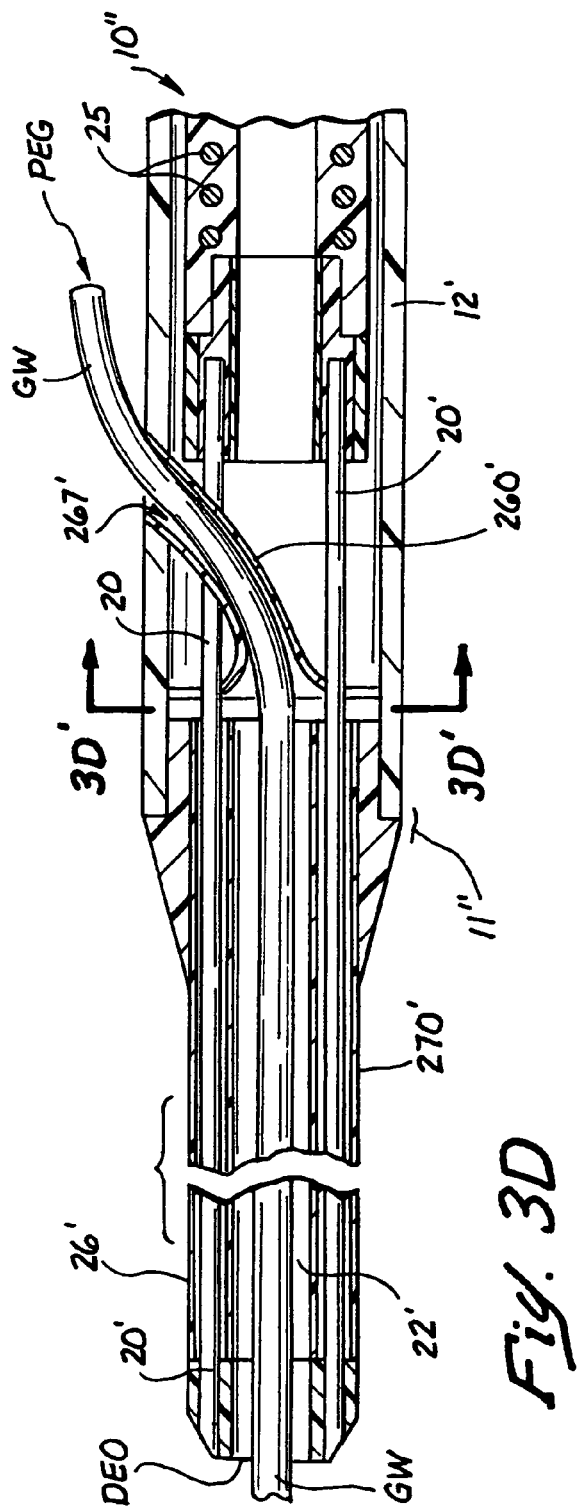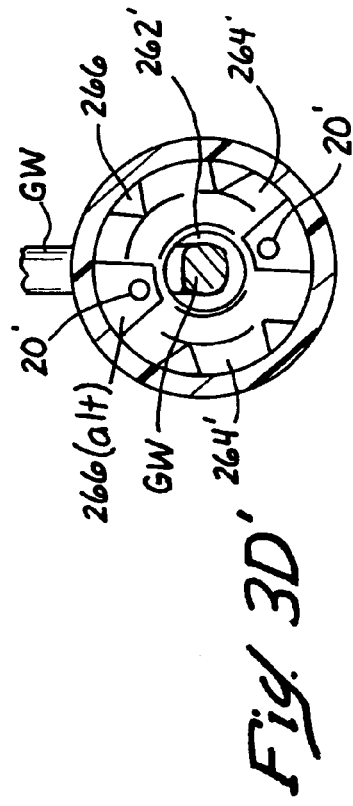

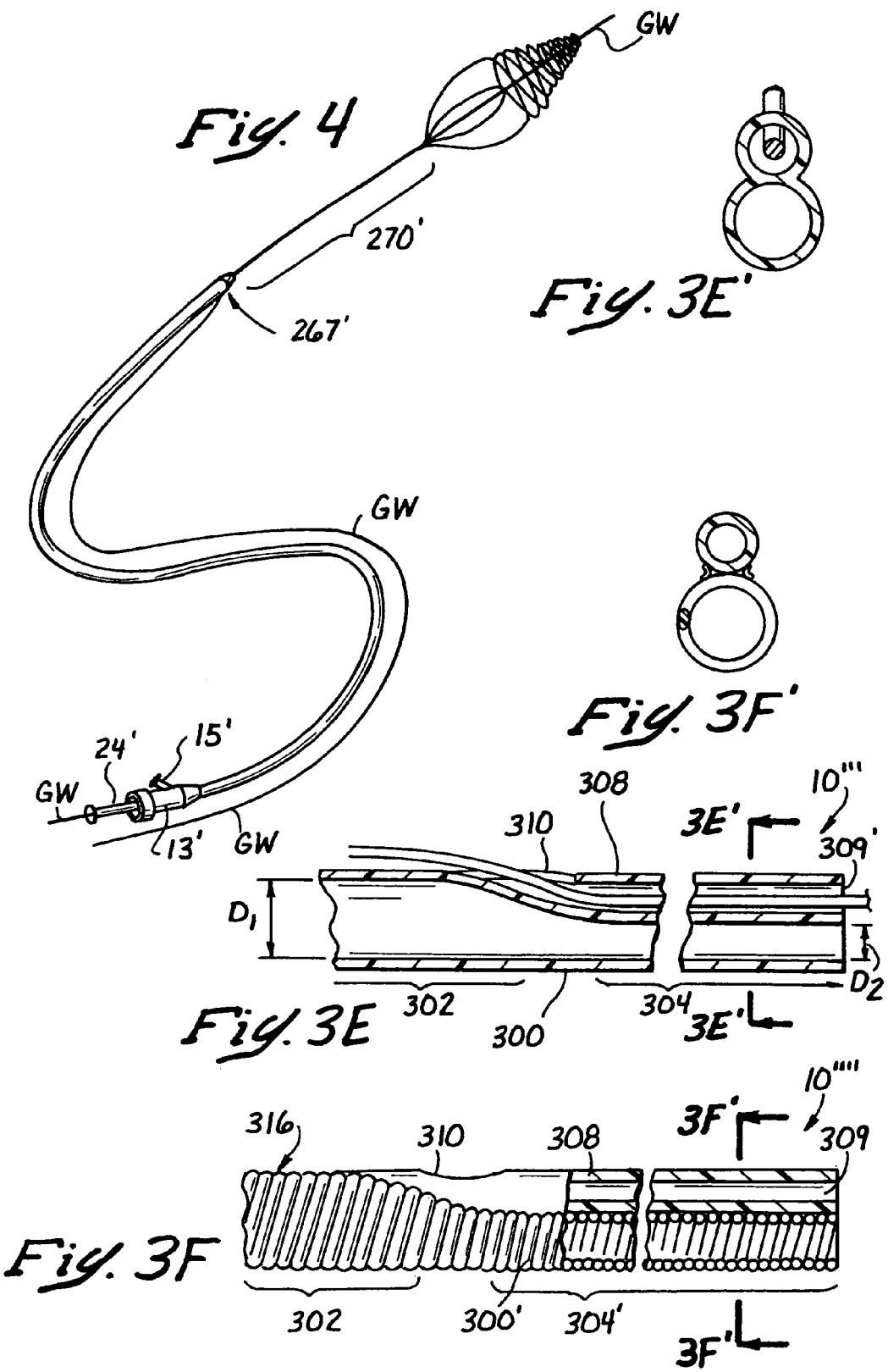

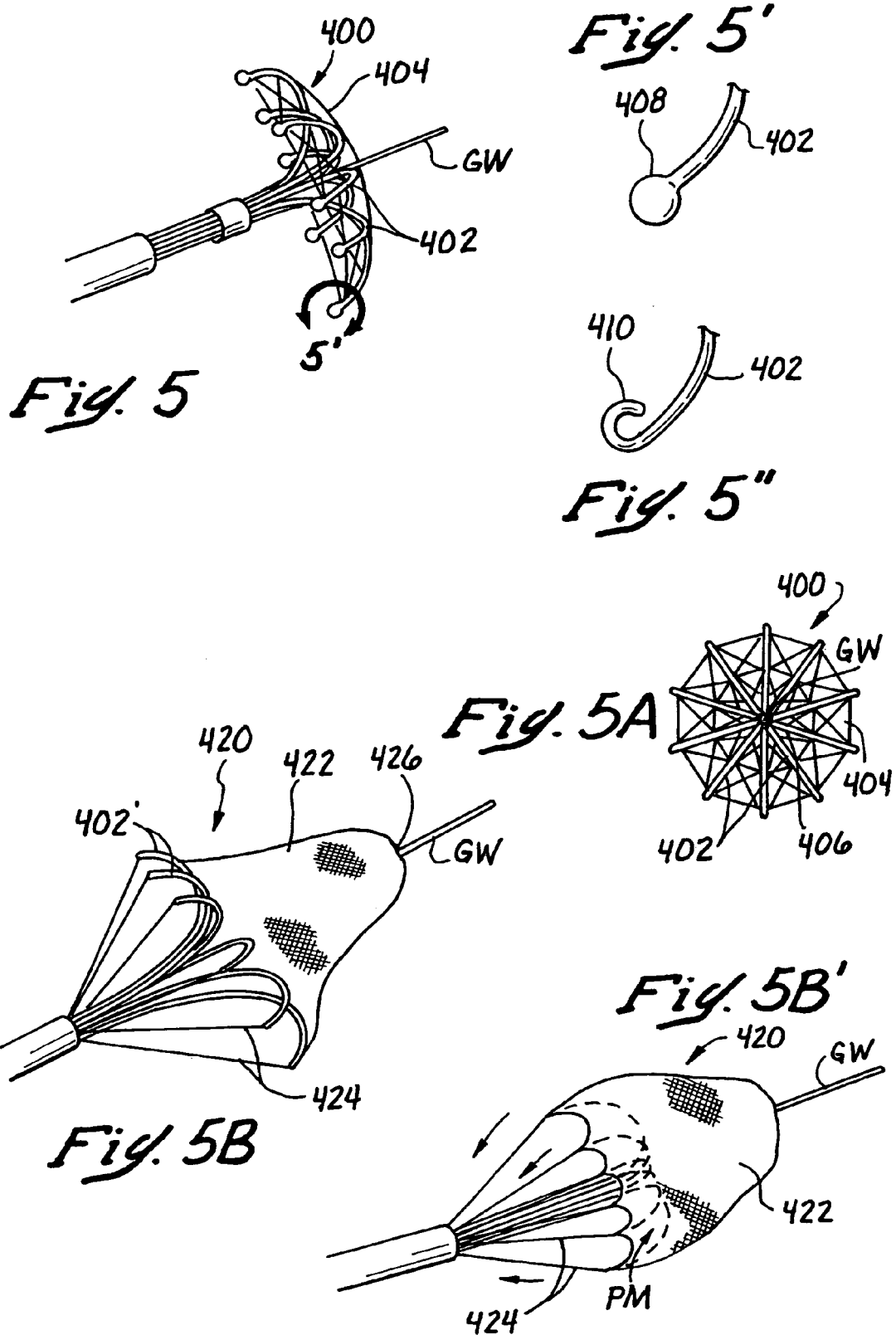

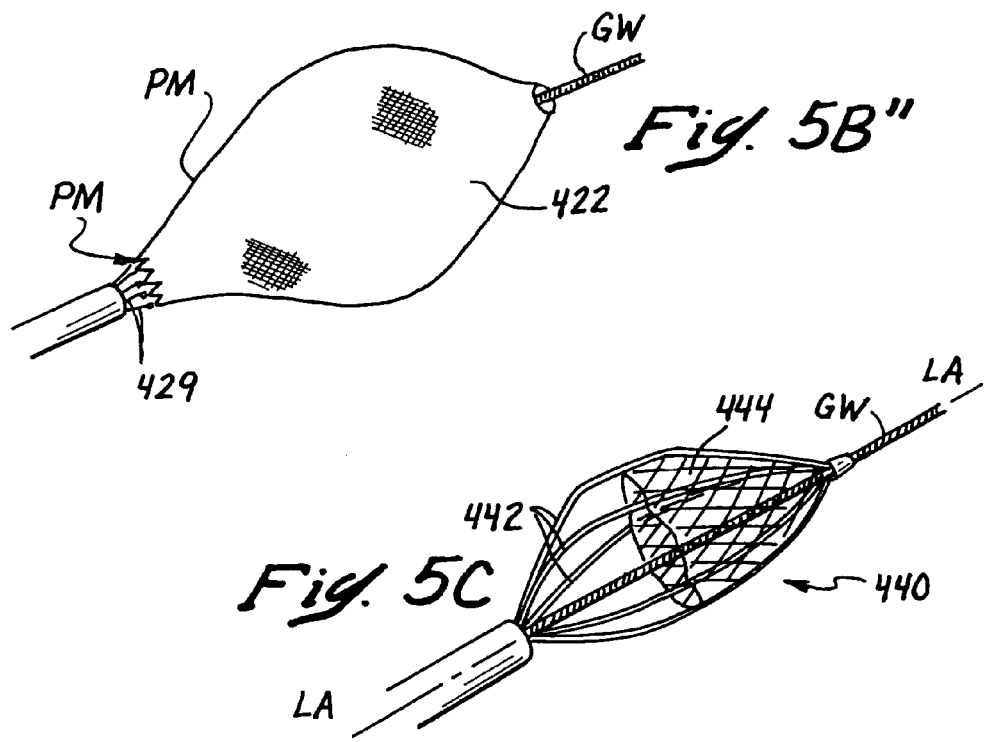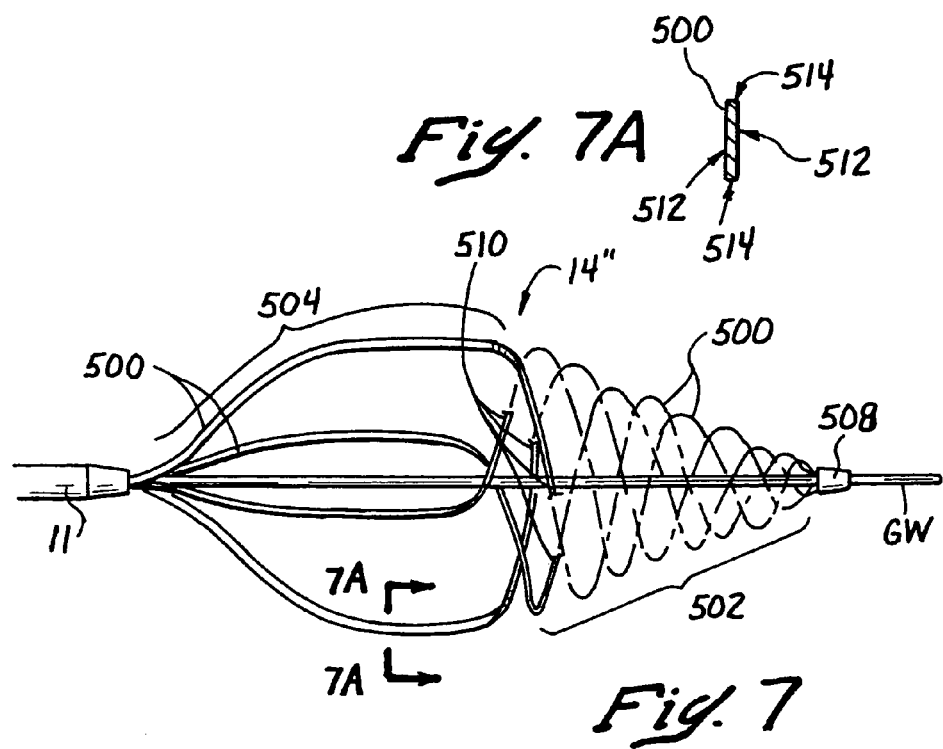

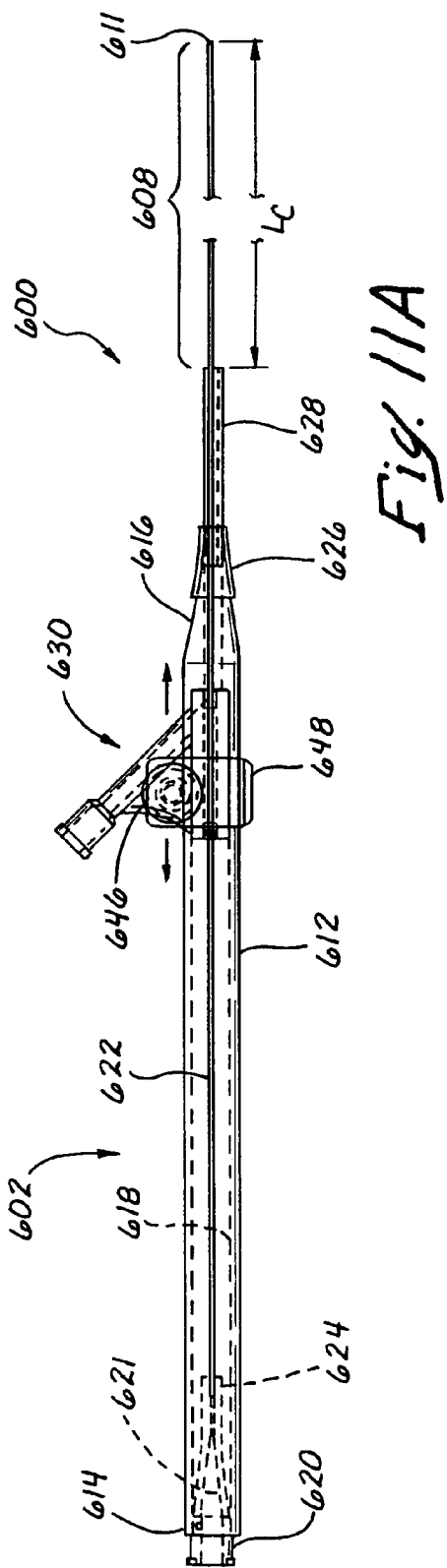
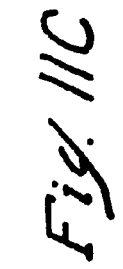
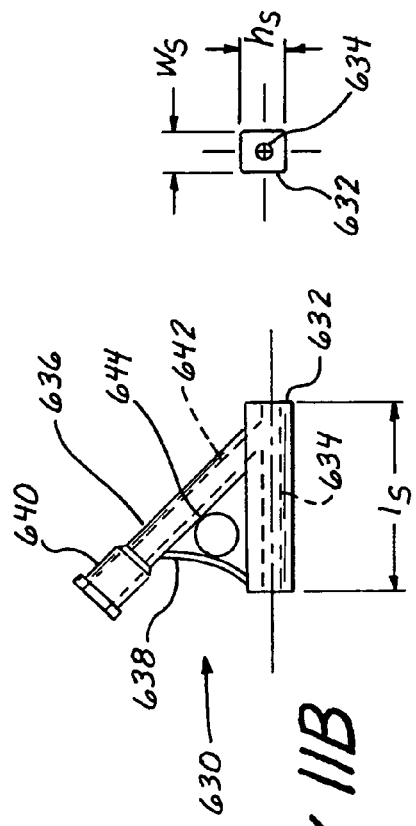
Fig. 11A
Fig. 11B
Fig. 11C

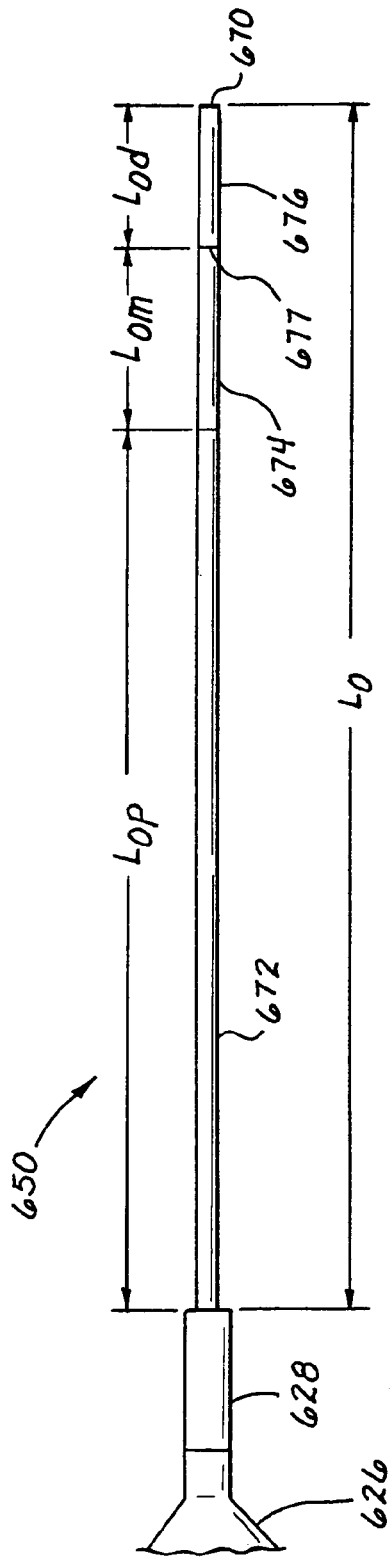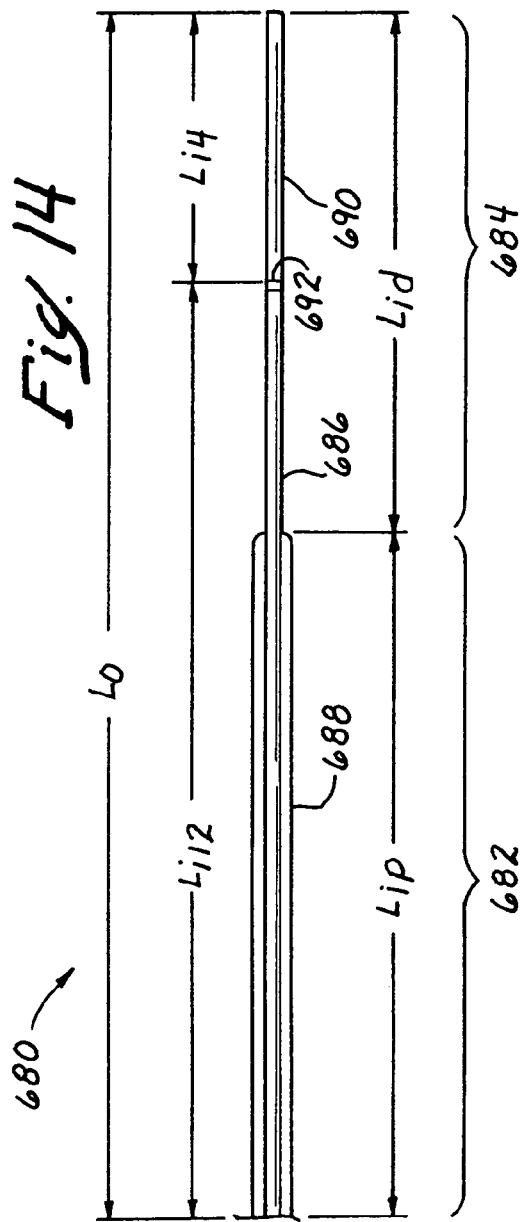

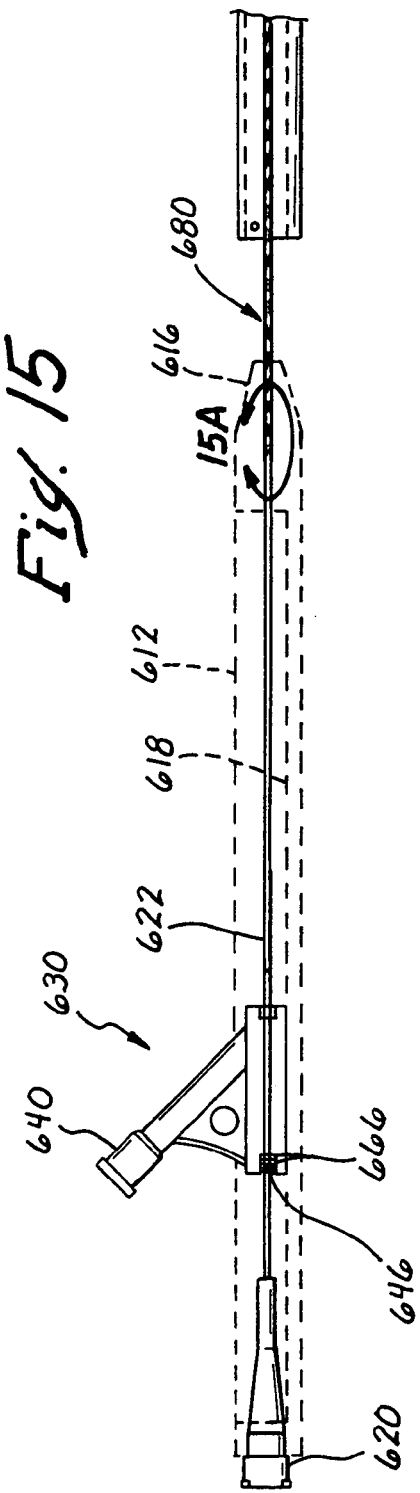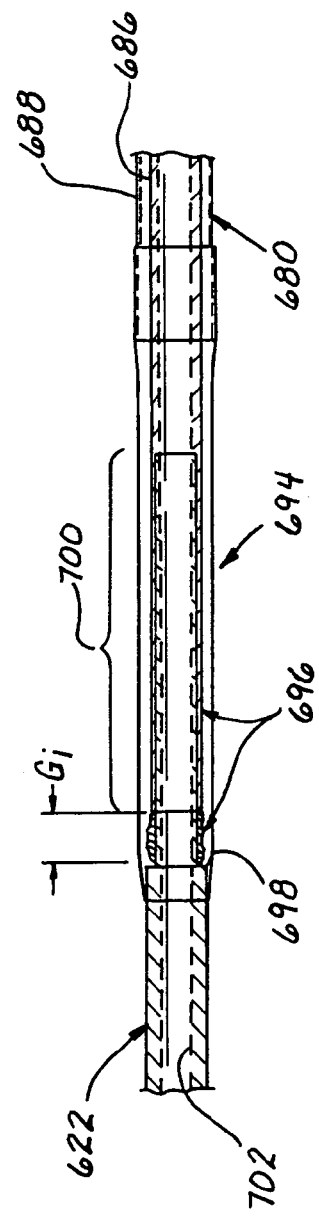

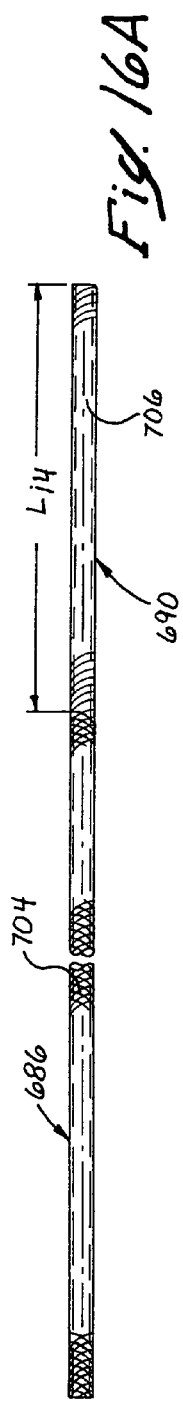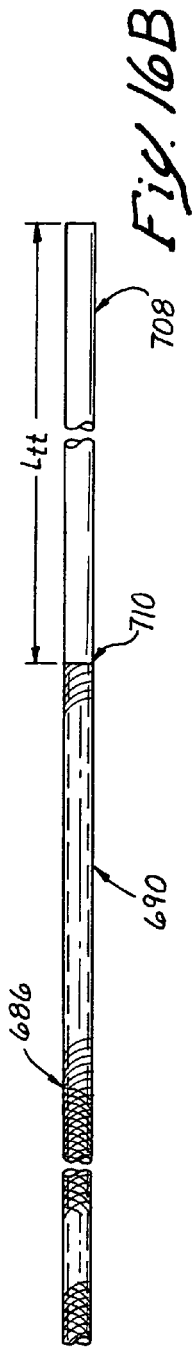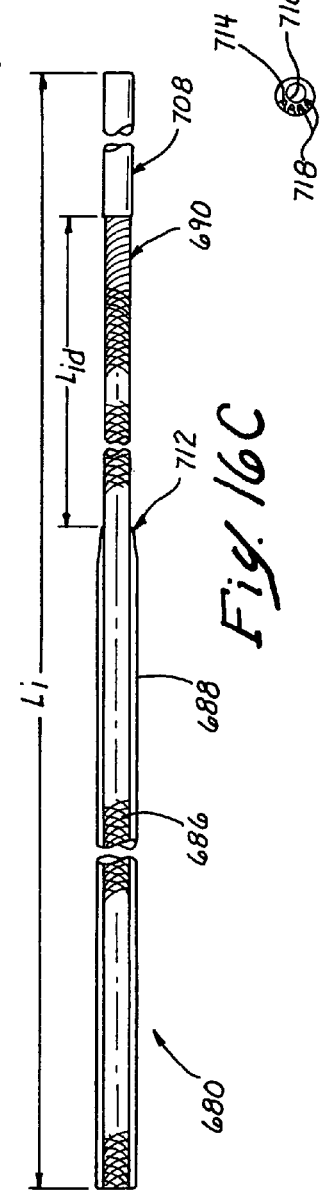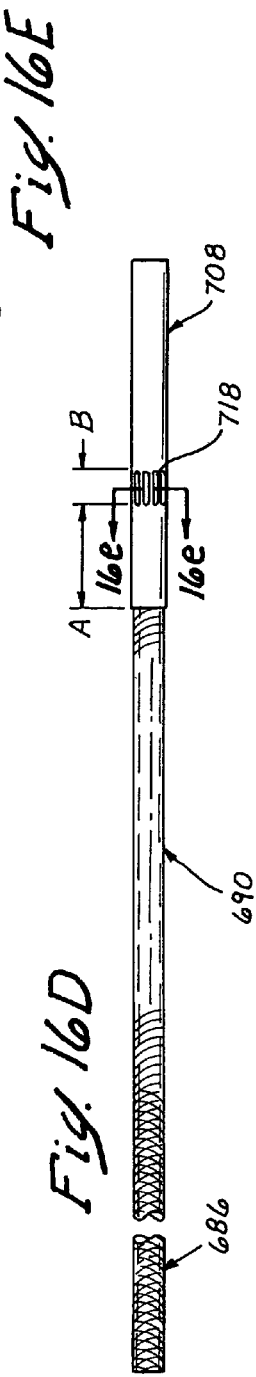
Fig. 16A
Fig. 16B
Fig. 16C
Fig. 16D
Fig. 16E

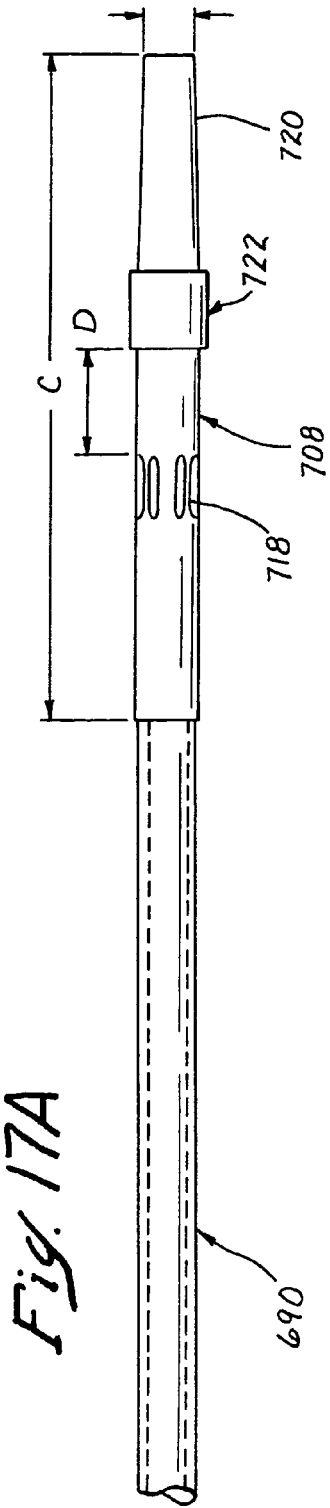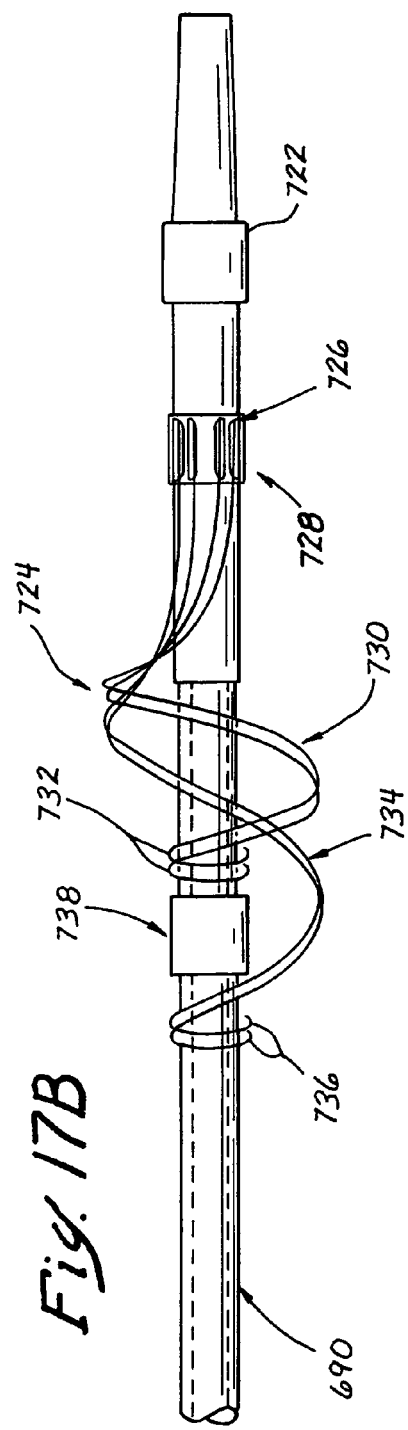

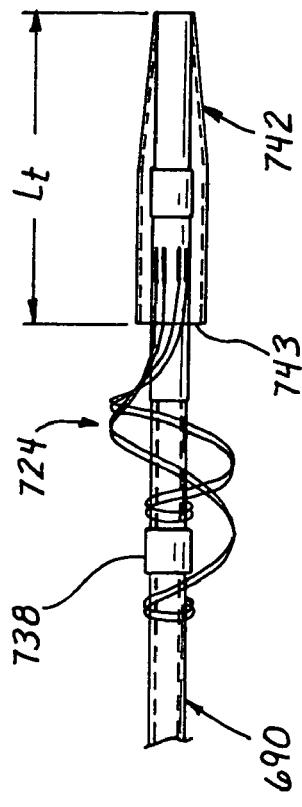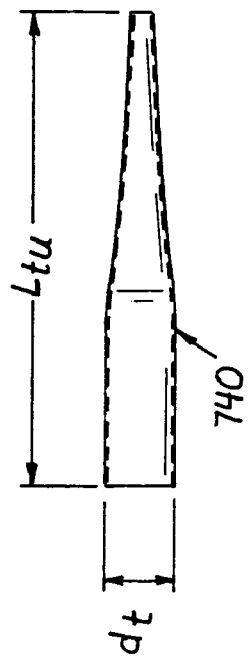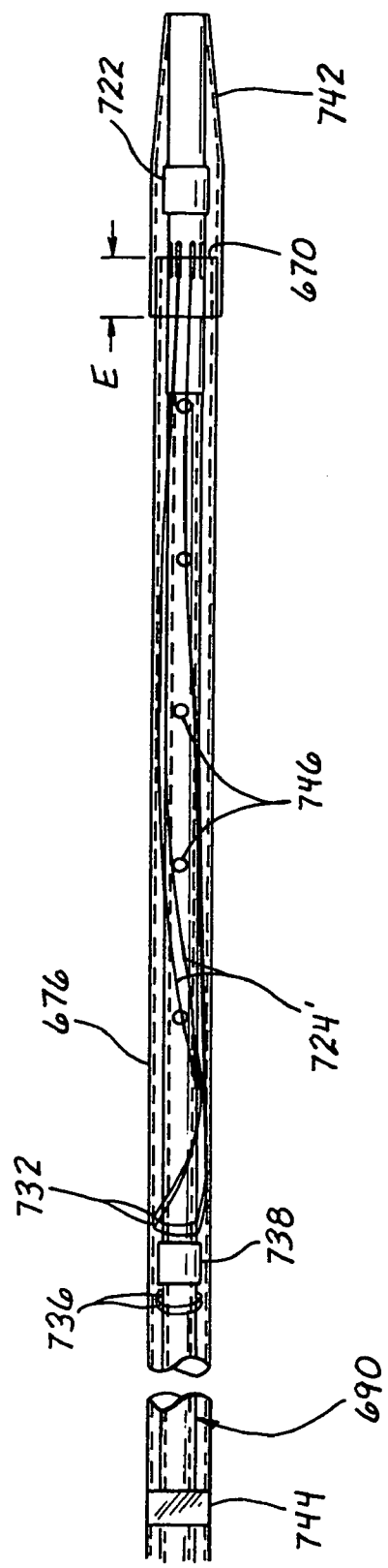

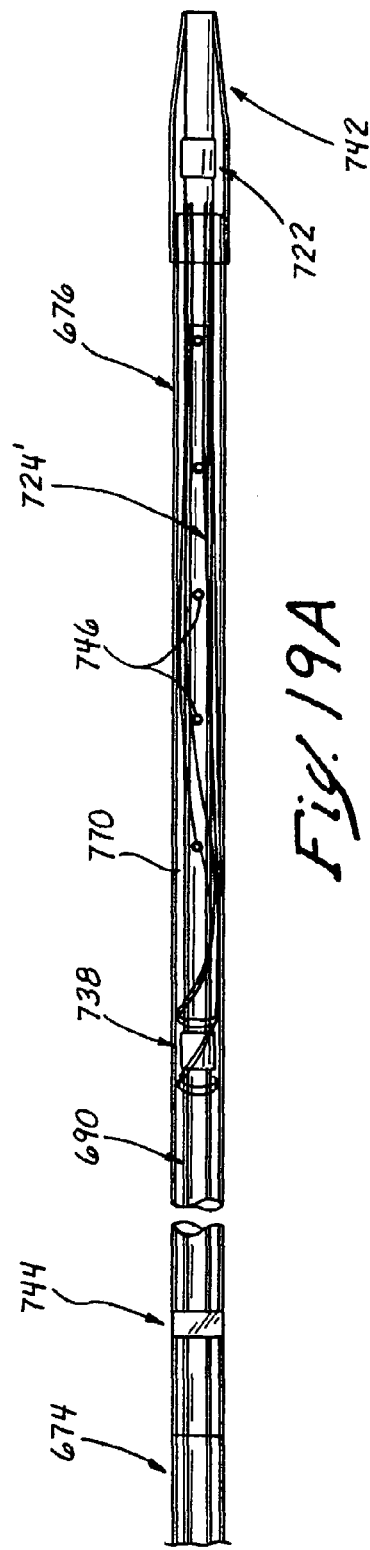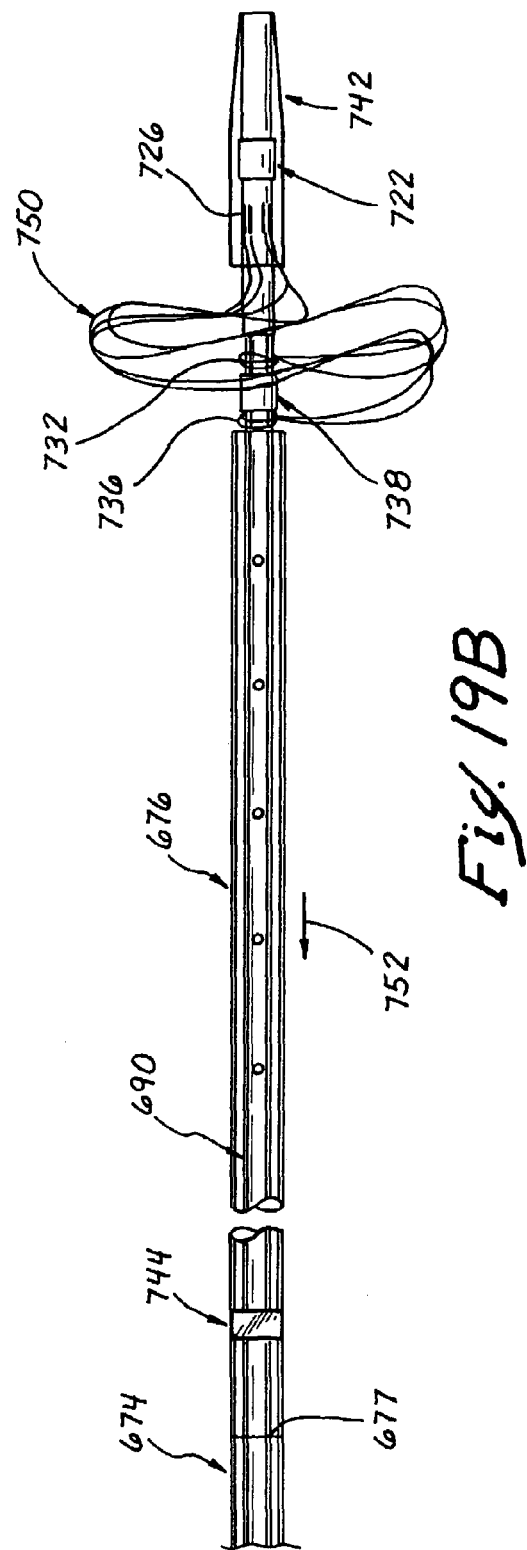

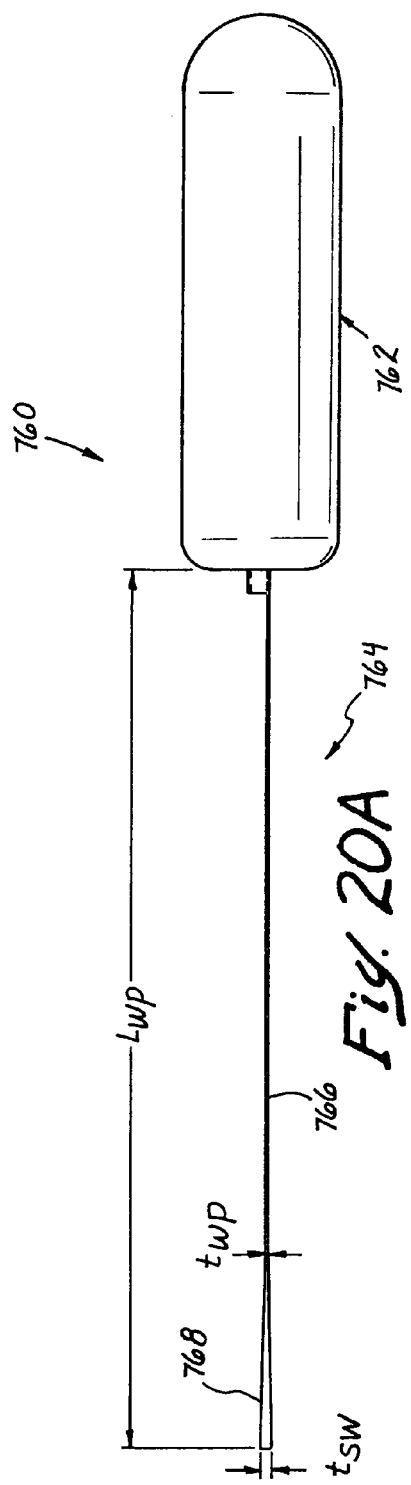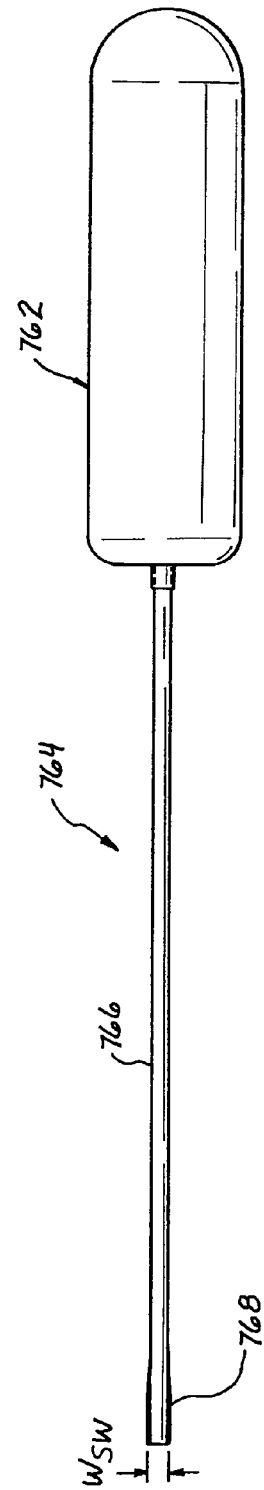

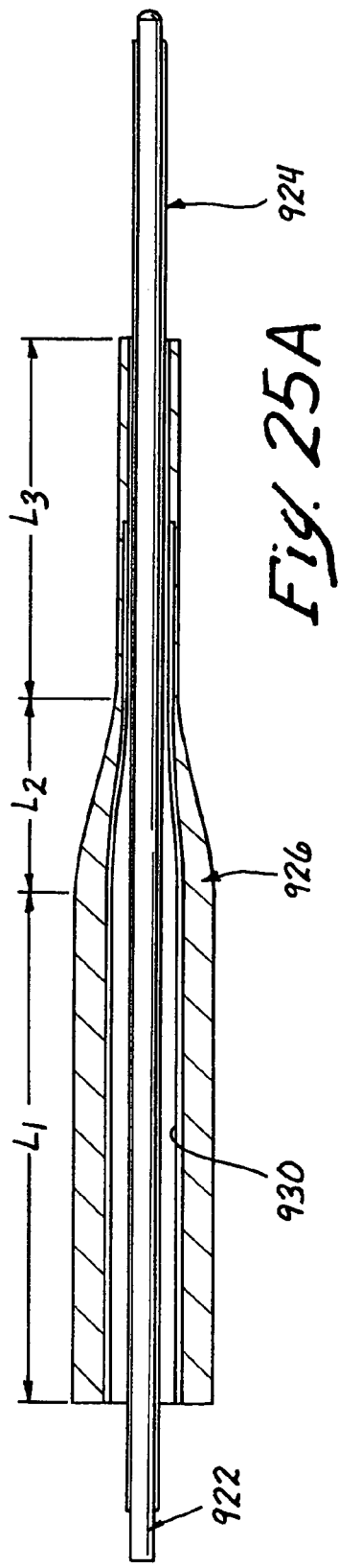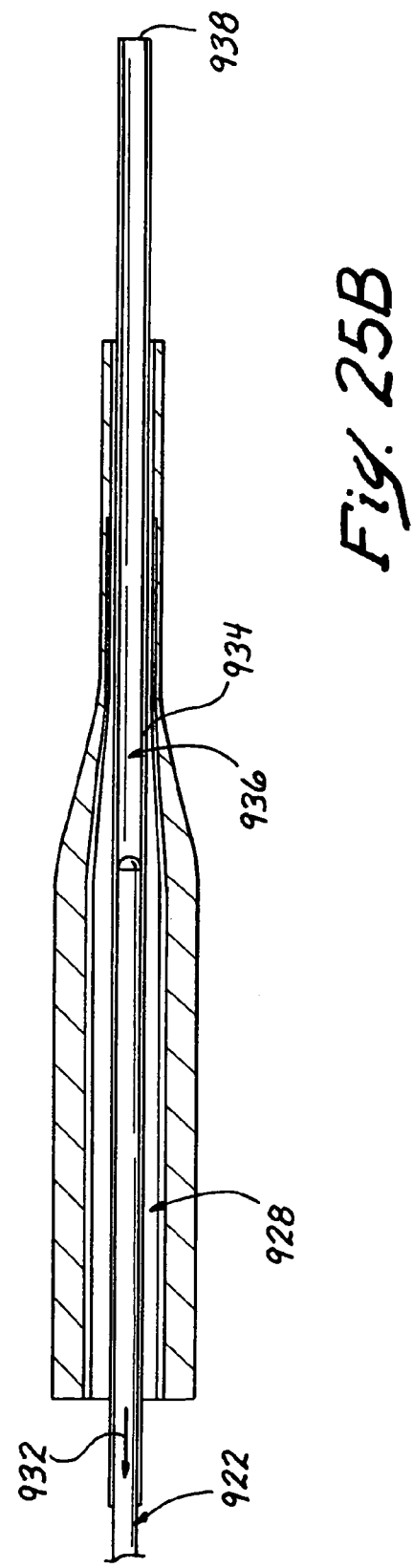

EMBOLECTOMY CATHETERS AND METHODS FOR TREATING STROKE AND OTHER SMALL VESSEL THROMBOEMBOLIC DISORDERS

This is a continuation of application Ser. No. 09/437,530 filed Nov. 10, 1999 now U.S. Pat. No. 6,685,722 which is a continuation-in-part of application of Ser. No. 09/071,561 filed on May 1, 1998 and now issued as U.S. Pat. No. 6,511,492 on Jan. 28, 2003

FIELD OF THE INVENTION

The present invention relates generally to medical methods and devices, and more particularly to thrombolectomy catheters, and methods for using such catheters, for removing blood clots or other matter from the lumens of blood vessels or other anatomical conduits.

BACKGROUND OF THE INVENTION

Various types of thromboembolic disorders, such as stroke, pulmonary embolism, peripheral thrombosis, atherosclerosis, and the like, are known to occur in human beings and other mammals. Such thromboembolic disorders are typically characterized by the presence of a thromboembolus (i.e., a viscoelastic blood clot comprised of platelets, fibrinogen and other clotting proteins) which has become lodged at a specific location in a blood vessel.

In cases where the thromboembolism is located in a vein, the obstruction created by the thromboembolus may give rise to a condition of blood stasis, with the development of a condition known as thrombophlebitis within the vein. Moreover, peripheral venous embolisms may migrate to other areas of the body where even more serious untoward effects can result. For example, the majority of pulmonary embolisms are caused by emboli that originate in the peripheral venous system, and which subsequently migrate through the venous vasculature and become lodged with the lung.

In cases where the thromboembolus is located within an artery, the normal flow of arterial blood may be blocked or disrupted, and tissue ischemia (lack of available oxygen and nutrients required by the tissue) may develop. In such cases, if the thromboembolism is not relieved, the ischemic tissue may become infarcted (i.e., necrotic). Depending on the type and location of the arterial thromboembolus, such tissue infarction can result in death and amputation of a limb, myocardial infarction, or stroke. Notably, strokes caused by thromboemboli which become lodged in the small blood vessels of the brain continue to be a leading cause of death and disability, throughout the world.

In modern medical practice, thromboembolic disorders are typically treated by one or more of the following treatment modalities:

a) pharmacologic treatment wherein thrombolytic agents (e.g., streptokinase, urokinase, tissue plasminogen activator (TPA)) and/or anticoagulant drugs (e.g., heparin, warfarin) are administered in an effort to dissolve and prevent further growth of the clot;

b) open surgical procedures (e.g., surgical embolectomy or clot removal) wherein an incision is made in the blood vessel in which the clot is lodged and the clot is removed through such incision—sometimes with the aid of a balloon-tipped catheter (e.g., a "Fogarty Catheter") which is passed through the incision and into the lumen of the blood vessel where its balloon is inflated and used to extract the clot out of the incision; and, c) transluminal catheter-based interventional procedures wherein a clot removing/disrupting catheter (e.g., a suction-type catheter having a suction tip, clot-capturing type catheter having a clot capturing receptacle (e.g., a basket, coil, hook, etc.), or clot-disrupting catheter having a clot disrupting apparatus (e.g., an ultrasound probe or laser)) is percutaneously inserted and advanced through the patient's vasculature to a location adjacent the clot. The suction tip, clot capturing receptacle or clot disrupting apparatus is used to aspirate, capture & remove, disrupt or ablate the offending clot.

Each of the above-listed treatment modalities has its own set of advantages and disadvantages. For example, pharmacologic treatment has the advantage of being non-invasive and is often effective in lysing or dissolving the clot. However, the thrombolytic and/or anticoagulant drugs used in these pharmacologic treatments can cause untoward side effects such as bleeding or hemorrhage. Also, in cases where time is of the essence, such as cases where an arterial thromboembolism is causing severe tissue ischemia (e.g., an evolving stroke or an evolving myocardial infarction) the time which may be required for the thrombolytic drugs to fully lyse or dissolve the blood clot and restore arterial blood flow may be too long to avoid or minimize the impending infarction.

Open surgical thrombus-removing procedures can, in many cases, be used to rapidly remove clots from the lumens of blood vessels, but such open surgical procedures are notoriously invasive, often require general anesthesia, and the use of such open surgical procedures is generally limited to blood vessels which are located in surgically accessible areas of the body. For example, many patients suffer strokes due to the lodging of blood clots in small arteries located in surgically inaccessible areas of their brains and, thus, are not candidates for open surgical treatment.

Transluminal, catheter-based interventional procedures are minimally invasive, can often be performed without general anesthesia, and can in some cases be used to rapidly remove a clot from the lumen of a blood vessel. However, such catheter-based interventional procedures are highly operator-skill-dependent, and can be difficult or impossible to perform in small or tortuous blood vessels. Thus, patients who suffer strokes due to the presence of clots in the small, tortuous arteries of their brains may not presently be candidates for catheter-based, transluminal removal of the clot, due to the small size and tortuosity of the arteries in which their clots are located.

In concept, the trasluminally deployable clot capturing type of catheters could be useable in ischemic strokes, because they are typically capable of removing an offending blood clot without the need for suction or application of energy (e.g., laser, ultrasound) which could be injurious to the delicate, small blood vessels of the brain. However, none of the prior art trasluminally deployable clot capturing type of catheters are believed to be of optimal design for use in the small blood vessels of the brain because they are a) not equipped with appropriate guidewire passage lumens to allow them to be passed over previously inserted, small-diameter (e.g., 0.006-0.018 inch) guidewires, b) they are not adapted for rapid exchange over a guidewire of standard length (e.g., a guidewire which is less than twice the length of the catheter) and c) the clot capturing receptacles of these catheters are not optimally constructed and configured for removal of clots from very small blood vessels as are typically found in the brain.

Examples of trasluminally deployable clot-capturing type embolectomy catheters of the prior art include those described in U.S. Pat. No. 4,706,671 (Weinrib), U.S. Pat. No.

4,873,978 (Ginsburg), U.S. Pat. No. 5,011,488 (Ginsburg), and U.S. Pat. No. 5,895,398 (Wensel, et al.). The '390 patent to Wetzel, et al., discloses a clot capture device where a small catheter is first passed in a distal direction through a viscoelastic clot. A clot capture coil mounted to a stiff insertion mandrel is then advanced through the catheter and deployed on the distal side of the clot. The clot capture coil may be a plurality of wires having shape memory which radially expand into a variety of shapes that, when the insertion mandrel is retracted, ensnare the clot for removal. Despite extensive development in this area, for the reasons stated above and/or other reasons, none of the prior art embolectomy catheters are believed to be optimally designed for treating ischemic stroke.

Thus, there exists a need for the development of a new transluminally insertable, clot-capturing type embolectomy catheters which are advanceable and exchangeable over preinserted small diameter guidewires, and which are constructed to rapidly and selectively remove blood clots or other matter from small, delicate blood vessels of the brain, so as to provide an effective treatment for evolving strokes and other thromboembolic disorders.

SUMMARY OF THE INVENTION

The present invention generally comprises an embolectomy catheter device and method for removing blood clots or other matter from the lumens of blood vessels or other anatomical conduits of a mammalian body. The embolectomy catheters and methods of the present invention are particularly suitable for use in removing clots or thromboemboli from small arteries of the mammalian brain to prevent or minimize the severity of stroke.

A. Embolectomy Catheters of the Present Invention

In one aspect of the present invention, an embolectomy catheter for removing a blood clot or other such obstructive matter from a blood vessel is provided. The embolectomy catheter includes an elongate flexible catheter body having a proximal end, a distal end, an inner tube, and a guidewire lumen a part of which extends longitudinally through the inner tube. A clot removal device on the inner tube is deployable in a first state to a radially expanded configuration. A guidewire is sized to passed through the inner tube and project distally from the distal end of catheter body.

The catheter desirably includes an outer tube arranged to surround and constrain the clot removal device about the inner tube in a second state prior to its deployment to the first state. Both the catheter body and the clot removal device are passable through the clot in the second state. The catheter also may include a handle whereby an insertion portion of the catheter body extends distally from handle. The insertion portion includes the inner tube and outer tube, both extending substantially to the distal end of the catheter body. The inner and outer tubes are preferably relatively axially displaceable to cause the clot removal device to transition between the first and second state.

In a preferred embodiment, the clot removal device has a proximal end and a distal end, the distal end being attached to the inner tube and the proximal end being free to slide axially over the inner tube. The proximal end of the clot removal device is axially displaced away from the distal end within the outer tube so as to longitudinally stretch and radially constrain the device in the second state prior to its deployment to the first state. The clot removal device may take a variety of forms, but is preferably a plurality of separate wires attached at their distal ends to the inner tube and helically wound or looped about the inner tube at their proximal ends. In the first, deployed state, the plurality of helically wound wires radially expands into a tangled nest which is suitable for capturing the clot. Desirably, a marker band is arranged to slide longitudinally with the proximal end of clot removal device to indicate to operator the deployment state. Marker bands on both the inner and outer tubes provide further relative position indications.

In accordance with a further aspect of the invention, an embolectomy catheter for removing a blood clot or other such obstructive matter from a blood vessel comprises an elongate flexible catheter body having a proximal end, a distal end, an axis extending from a proximal end to the distal end, an inner tube, and an outer tube terminating just short of a distal end of catheter body. The clot removal device on the inner tube is initially collapsed and constrained in its collapse configuration by a portion of the outer tube. A distal tip of the catheter body located on the inner tube is adapted to pass through the blood clot to be removed. The outer tube is axially retractable to remove the constraint on the clot removal device such that it may radially expand to a deployed configuration.

Preferably, the outer tube extends distally within a proximal mouth of the distal tip prior to being retracted. The inner tube may be reinforced along its entire length, and is preferably more flexible at its distal end than at its proximal end. In addition, both the inner and outer tubes may include discrete segments that become more flexible in a direction from the proximal end to the distal end. In one embodiment, the catheter body has a size of between approximately 1-5 French at its distal end, and is preferably about 3 French.

A further aspect of present invention includes a handle attached to a proximal end of an insertion portion of catheter body. An actuator is provided on handle for proximally displacing the outer tube with respect to the inner tube in order to deploy the clot removal device. In one embodiment, the actuator comprises a slide movable along the handle and attached to the outer tube, the slide including a through bore for receiving an extension of the inner tube. An infusion port on the slide enables infusion of fluid in the annular space between the inner and outer tubes.

A further embolectomy catheter device of the present invention generally comprises; a) an elongate, pliable clot penetrating catheter which is advanceable, distal end first, through the clot or other obstructive matter (e.g., thrombus, thromboembolus, pieces of detached atherosclerotic plaque, foreign matter, etc.) which is to be removed, and b) a matter capturing receptacle which is deployable from the distal end of the catheter after it has been advanced through the obstructive matter, to capture and facilitate removal of the obstructive matter. The matter capturing receptacle is initially disposed in a first or stowed configuration wherein the receptacle is in a radially collapsed condition and contained upon or within the catheter or otherwise sufficiently compact to pass through the clot or other obstructive matter. Thereafter, the matter capturing receptacle is deployable (e.g., advanceable, projectable and/or expandable) from the catheter such that it assumes a second or expanded configuration wherein the receptacle may receive and at least partially surround the distal aspect of the clot or other obstructive matter so as to facilitate extraction and removal of the blood clot or other obstructive matter along with the catheter.

A guidewire lumen may extend longitudinally through the entire length of the catheter (i.e., an "over-the-wire" embodiment) or through only a distal portion of the catheter (i.e., a "rapid exchange" embodiment). In either of these embodiments of the catheter, the guidewire lumen may extend through the matter capturing receptacle such that the catheter (with its matter capturing receptacle in its collapsed or stowed configuration) may be advanced over a guidewire which has previously been passed through the vessel-obstructing clot or other obstructive matter. Such arrangement of the guidewire lumen additionally allows the embolectomy catheter to be exchanged (e.g., removed and replaced with another embolectomy catheter or another type of catheter) if such exchange should become necessary or desirable. This ability to allow the guidewire to remain positioned through the offending clot or other obstructive matter may serve to ensure that the catheter or its replacement can be re-advanced through the clot or other obstructive matter to its desired position.

The matter capturing receptacle of the catheter may comprise a distal obstructive matter-engaging portion (e.g., a coil, basket or concave member) of porous construction (e.g., a woven, coiled or mesh structure formed of wire, fiber or fabric), which is attached to the catheter by way of one or more proximal struts (e.g. connector members (e.g., a plurality of thin wires or struts). Initially, with the matter capturing receptacle disposed in its first (e.g., collapsed or stowed) configuration, the distal end of the catheter is advanced through the clot or other obstructive matter. After the catheter has been advanced through the clot or other obstructive matter, the matter capturing receptacle is moved to its second (e.g., expanded or operative) configuration, such that the distal obstructive matter-engaging portion of the receptacle will contact and/or at least partially surround the distal aspect of the clot or other obstructive matter. The distal obstructive matter-engaging portion of the receptacle is preferably of permeable construction to permit blood to flow therethrough, but is sufficiently dense (i.e., sufficiently impermeable) to prevent the clot or other obstructive matter from passing therethrough. In this manner, the distal obstructive matter-engaging portion of the receptacle is useable to retract or draw the clot or other obstructive matter, in the proximal direction, from its then-present location. The proximal strut(s) which extend between the receptacle to the catheter are typically of radially splayed or outwardly angled configuration and is/are preferably configured, oriented and positioned so as to slice, cut or otherwise pass through the matter of the clot or other obstructive matter, when deployed at a site distal to the clot or other obstructive matter and subsequently retracted in the proximal direction. To assist such proximal strut(s) in passing through the clot or other obstructive matter, energy (e.g., radio-frequency energy, vibration, heat, etc.) may be applied to the proximal strut(s) during their proximal retraction through the clot or other obstructive matter.

A contrast medium injection port may be formed on the proximal portion of the embolectomy catheter, to allow radiographic contrast medium (e.g., dye) to be injected through the catheter while a guidewire remains positioned within the guidewire lumen.

B. Rapid Exchange Microcatheter Useable in Conjunction with Embolectomy Catheters of the Present Invention Further in accordance with the present invention, there is provided a rapid exchange microcatheter which comprises a small diameter flexible microcatheter of a type commonly used in neuroradiology procedures (e.g., Prowler™ microcatheter, Cordis Endovascular Systems, Miami Lakes, Fla.), which has greater flexibility at or near its distal end than at or near its proximal end, and which includes in accordance with this invention, the addition of a guidewire passage port formed in the sidewall of the catheter, at a spaced distance (e.g., 0.5-35 cm) from its distal tip. A guidewire deflector may be formed within the main lumen of the catheter adjacent to the guidewire passage aperture, to deflect the proximal end of a guidewire out of the guidewire passage aperture as the catheter is advanced over the guidewire. The formation of such guidewire passage aperture and guidewire deflector allows a guidewire to be passed through only a distal portion of the catheter lumen. This lumen arrangement allows the microcatheter to be exchanged (i.e., removed and replaced by another microcatheter or an embolectomy catheter of the above-summarized design) while the operator holds the guidewire in place by grasping the exteriorized proximal end of the guidewire—even in instances where a standard length guidewire (i.e., not an "exchange-length" guidewire) is used.

C. Methods of the Present Invention for Removing Clots or Other Matter from Blood Vessels The present invention also contemplates methods of removing clots or other obstructive matter from blood vessels. One method includes the use of a guidewire to first pierce and traverse at least portion of the clot to be removed. An embolectomy catheter of the present invention is advanced either with or over the guidewire and through the clot. A clot removal device provided on the catheter is then deployed radially outwardly, and the catheter retracted to entangle the clot removal device with the clot. Further retraction of the catheter in combination with optional suction removes the clot.

In a further method of the present invention, the guidewire includes an infusion lumen therein. After the guidewire is inserted through the clot, medication or clot dissolution fluid may be administered to the distal side of the clot. Alternatively, visualization fluid may be injected to obtain a better picture of the clot from the distal side thereof.

Further in accordance with the present invention, there are provided a method for treating ischemic stroke caused by a thromboembolism which has become lodged in a small blood vessel of the brain (i.e., blood vessels located in, on or around the brain). The method of the present invention may be carried out using the rapid exchange microcatheters and embolectomy catheters of the present invention. An exemplary method generally comprises the steps of:

A. percutaneously inserting a guidewire (alone or in combination with a guide catheter) into an intracranial blood vessel, using the Seldinger technique or other appropriate method of percutaneous guidewire placement;

B. advancing a microcatheter over the guidewire, or separately from the guidewire, through the vasculature until the microcatheter is near the site at which the blood clot or other obstructive matter is located;

C. passing radiographic contrast medium (e.g., dye) through the microcatheter under radiographic visualization to verify the exact location of the obstructive matter and/or to map the vascular anatomy in the area of the obstruction;

D. advancing the guidewire (or a separate small guidewire) through the microcatheter until such guidewire becomes located in a desired operative position relative to the obstructive matter (e.g., such that its distal end has fully or partially traversed or passed through the thromboembolism or other obstructive matter);

E. withdrawing and removing the microcatheter while substantially maintaining the small guidewire in its operative position (e.g., preventing the guidewire from moving so far as to lose the access to the obstructive matter that the presence of the guidewire provides);

F. advancing a matter-capturing type embolectomy catheter (such as an embolectomy catheter of the present invention) which has an obstructive matter-capturing receptacle deployable therefrom, over the operatively positioned guidewire until the distal end of the embolectomy catheter has advanced fully or at least partially through the obstructive matter (e.g., has penetrated through an obstructive thromboembolism);

G. optionally injecting radiographic contrast medium through a lumen of the embolectomy catheter to guide or verify the positioning of the embolectomy catheter relative to the lodged blood clot or other obstructive matter;

H. deploying the obstructive matter-capturing receptacle of the embolectomy catheter such that it assumes its second or expanded configuration at a site which is distal (i.e., downstream) of the lodged blood clot or other obstructive matter;

I. retracting the obstructive matter-capturing receptacle such that a proximal portion of the receptacle (i.e., proximal struts) passes through the thromboembolism and at least a portion of the clot or other obstructive matter becomes located within the obstructive matter-receiving portion of the obstructive matter-capturing receptacle;

J. optionally injecting radiographic contrast to medium through a lumen of the embolectomy catheter to determine whether blood flow has been restored through the region of the blood vessel which had previously been deprived of blood flow due to the presence of the clot or other obstructive matter; and, K. retracting the embolectomy catheter to remove the blood clot or other obstructive matter from the body (e.g., withdrawing the embolectomy catheter and the extracted clot or other obstructive matter through the percutaneous entry tract through which the catheter had previously been inserted).

Thus, by the above-summarized method of the present invention, the blood clot or other obstructive matter which is causing an ischemic (i.e., thrombotic or embolic) stroke is removed and arterial blood flow is restored to the region of the brain which had become ischemic due to the lodging on the offending blood clot or other obstructive matter within the blood vessel.

D. Infusion Guidewire

An infusion guidewire of the present invention preferably comprises an inner wire and an outer sheath slideable thereover. The wire and sheath are first advanced together through the clot, and the inner wire is then retracted to open a lumen within the outer sheath. Advantageously, the outer sheath, or sheath and inner wire combination, can remain in place through the clot while different catheters are exchanged thereover.

Further elements, objects and advantages of the present invention will become apparent to those of skill in the art upon reading and understanding of the following detailed description of preferred embodiments and consideration of the accompanying drawings.

BRIEF DESCRIPTION OF THE DRAWINGS

FIG. 1 is a perspective view of a human patient having a first embodiment (an "over-the-wire" embodiment) of an embolectomy catheter of the present invention operatively inserted for the purpose of removing a blood clot or other obstructive matter from a small blood vessel of the brain.

FIG. 1A is a perspective view of the embolectomy catheter device of FIG. 1 operatively positioned upon a guidewire, and having its obstructive matter-capturing receptacle disposed in an expanded configuration.

FIG. 2A is an enlarged longitudinal sectional view of the distal end of the over-the-wire embolectomy catheter of FIG. 1 with its obstructive matter-capturing receptacle in a first or stowed position.

FIG. 2B is an enlarged, broken, longitudinal sectional view of the distal end of the over-the-wire embolectomy catheter of FIG. 1 with its obstructive matter-retrieving member in a distally advanced position and its obstructive matter-capturing receptacle disposed in a fully expanded configuration.

FIG. 2C is a cross-sectional view through line 2C-2C of FIG. 2A.

FIG. 2D is a cross-sectional view through line 2D-2D of FIG. 2A.

FIG. 2D' is a cross-sectional view through line 2D-2D of FIG. 2A, modified to show an alternative mode of constructing the guide bores in the distal tip member, through which the wires which form the obstructive matter-capturing receptacle extend.

FIG. 3A is an enlarged, broken, longitudinal sectional view of the distal end of the over-the-wire microcatheter of the prior art.

FIG. 3B is an enlarged, broken, longitudinal sectional view of the distal end of a second embodiment (i.e., another over-the-wire embodiment) of an embolectomy catheter of the present invention.

FIG. 3B' is a cross-sectional view through line 3B'-3B' of FIG. 3B.

FIG. 3C is an enlarged, broken, longitudinal sectional view of the distal end of a rapid exchange microcatheter of the present invention.

FIG. 3C' is a cross-sectional view through line 3C'-3C' of FIG. 3C.

FIG. 3D is an enlarged, broken, longitudinal sectional view of the distal end of a third embodiment (i.e., a rapid exchange embodiment) of an embolectomy catheter of the present invention.

FIG. 3D' is a cross-sectional view through line 3D'-3D' of FIG. 3D.

FIG. 3E is an enlarged, longitudinal sectional view of the distal end of a fourth embodiment (i.e., another rapid exchange embodiment) of an embolectomy catheter of the present invention.

FIG. 3E' is a cross-sectional view through line 3E'-3E' of FIG. 3E.

FIG. 3F is an enlarged, longitudinal sectional view of the distal end of a fifth embodiment (i.e., another rapid exchange embodiment) of an embolectomy catheter of the present invention.

FIG. 3F' is a cross-sectional view through line 3F'-3F' of FIG. 3F.

FIG. 4 is a perspective view of the third embodiment (i.e., a rapid exchange embodiment) of an embolectomy catheter of FIG. 3D having a guidewire operatively inserted through its guidewire lumen and its obstructive matter capturing receptacle in its deployed, radially expanded position.

FIG. 5 is a perspective view of a first alternative obstructive matter-capturing receptacle which may be incorporated into any of the embolectomy catheters of the present invention.

FIG. 5' is an enlarged view of portion 5' of FIG. 5.

FIG. 5" shows an alternative construction for portion 5' of FIG. 5.

FIG. 5A is a distal end view of FIG. 5.

FIG. 5B is a perspective view of a second alternative obstructive matter-capturing receptacle which may be incorporated into any of the embolectomy catheters of the present invention.

FIG. 5B' is a perspective view of the second alternative obstructive matter-capturing receptacle of FIG. 5B having a clot captured therewithin and with its support spines being partially retracted into the catheter.

FIG. 5B" is a perspective view of the second alternative obstructive matter-capturing receptacle of FIG. 5B having a clot captured therewithin and with its support spines being further retracted into the catheter so that the obstructive matter capturing receptacle is drawn partially around the captured clot.

FIG. 5C is a perspective view of a third alternative obstructive matter-capturing receptacle which may be incorporated into any of the embolectomy catheters of the present invention.

FIG. 6 is a perspective view of an optional guide catheter of the present invention having a proximal obstructive matter containment apparatus operatively deployed therefrom, and an embolectomy catheter of the present invention operatively inserted therethrough.

FIG. 7 is an elevational view of a variant of the helical basket type obstructive matter capturing receptacle of the catheters shown in FIGS. 1, 2B and 4, such variant being constructed of metal ribbon rather than wire.

FIG. 7A is a cross-sectional view through line 7A-7A of FIG. 7, illustrating the manner in which the metal ribbons may be twisted to enhance the ability of the proximal strut portions to the obstructive matter capturing receptacle to cut through the thromboembolic material.

FIG. 11A is an elevational view of the operating handle of FIG. 10 showing internal features in dashed line.

FIG. 11B is an isolated view of a sliding infusion port of the operating handle.

FIG. 11C is an end view of FIG. 11B.

FIG. 13 is a schematic view of outer tube of the embolectomy catheter of the present invention.

FIG. 14 is a schematic view of an inner tube of the embolectomy catheter of the present invention.

FIG. 15 is an elevational view of a proximal end of the catheter inner tube, with a proximal guidewire introducer, an inner hypotube, and the sliding infusion port mounted thereon.

FIG. 15A is a detailed sectional view of the junction between the inner hypotube and the proximal end of the catheter inner tube.

FIGS. 16A-16E are various views showing the structure and sequence of fabrication of the catheter inner tube.

FIG. 17A is an elevational view of the distal end of the catheter inner tube and a length of distal tip tubing having a radiopaque band mounted thereon.

FIG. 17B is an elevational view similar to FIG. 17A and showing the attachment of clot removal wires and a second radiopaque band.

FIG. 18A is an elevational view of a tapered tube prior to formation into a distal tip of the embolectomy catheter.

FIG. 18B is elevational view of the distal end of the catheter inner tube, much like FIG. 17B, and showing the distal tip mounted thereon.

FIG. 18C is an elevational view of a fully assembled distal end of the embolectomy catheter, showing internal features in dashed line.

FIG. 19A is a sectional view through the fully assembled distal end of the embolectomy catheter.

FIG. 19B is a sectional view similar to FIG. 19A, but showing the clot removal wires deployed to form a clot removal nest configuration.

FIG. 20A is elevational view of a fabrication tool for straightening the clot removal wires within the catheter outer tube.

FIG. 20B is a plan view of the fabrication tool of FIG. 20A.

FIG. 25A is a sectional view of the distal end of a catheter and an infusion guidewire of the present invention passing therethrough.

FIG. 25B is a sectional view similar to FIG. 25A and showing an inner wire being retracted from the infusion guidewire.

Figure 8A:
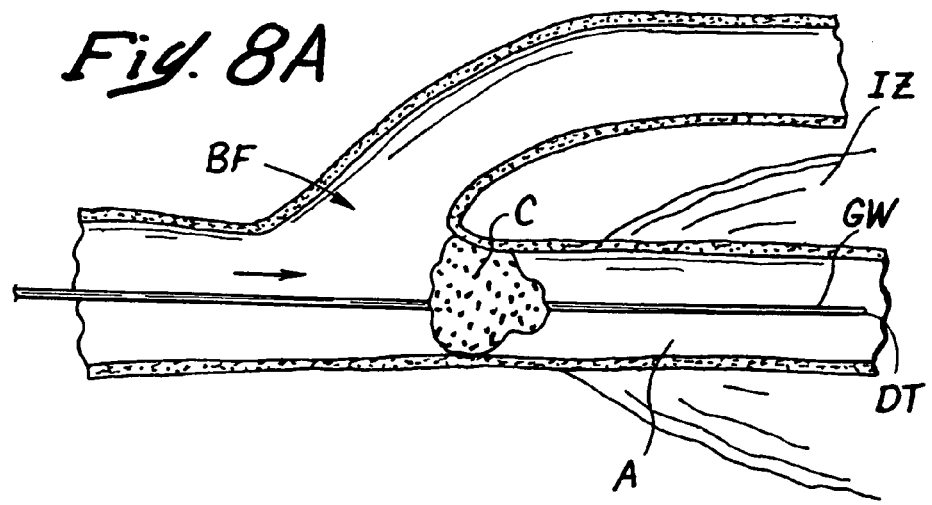
FIGS. 8A-8F are step-wise showings of a procedure wherein the first embodiment (i.e., an over-the-wire embodiment) of an embolectomy catheter of the present invention is used to remove a blood clot from a small blood vessel of a mammalian body.

The particular embodiments shown in these drawings, and additional embodiments of the invention, may now be better understood by reading and understanding the following detailed description wherein specific reference is made to the structures and steps illustrated or shown in the drawings.

DETAILED DESCRIPTION OF THE INVENTION

A. Over-The Wire Embodiments of the Embolectomy Catheter Device

Referring now to the drawings, wherein the showings are for the purpose of describing and illustrating exemplary embodiments of the present invention, and not for the purpose of limiting the scope of the invention, FIG. 1 shows a human patient in whom an over the wire embodiment of the embolectomy catheter device 10 of the present invention has been inserted for the purpose of removing a thromboembolus or blood clot from a small artery located in the patient's brain. Prior to introduction of the catheter device 10, the offending clot was located by angiography or other imaging means, and a small guidewire GW (e.g., a 0.010 in. Transend wire, Target/Boston Scientific catalog #46-802) was inserted into the patients femoral artery and advanced into the artery of the brain in which the clot is located, and through the clot. Thereafter, the catheter device 10 was advanced over the previously inserted guidewire GW to a position where the distal end of the catheter device 10 is near the clot. Alternatively, the guidewire is first placed into the catheter before insertion into the patient, and the catheter and guidewire are advanced together as a unit up to and through the clot.

First Embodiment

As shown in FIGS. 1-2D, the first embodiment of the over-the-wire catheter device 10 comprises an elongate, pliable catheter 11 having a clot capturing receptacle 14 deployable from its distal end DE, as shown. The obstructive matter-capturing receptacle 14 is formed of a plurality (e.g., 2 or more) wire members 20 which are initially retractable to substantially straight configurations and a first (i.e., stowed) position, within the catheter 11. (See FIG. 2A) When it is desired to deploy the obstructive matter capturing receptacle 14, the preformed wire members 20 are held stationary while the catheter 11 is retracted, or the wire members 20 are advanced in the distal direction while holding the catheter 11 stationary, such that the wires emerge from the constraint of the catheter 11 and resiliently assume a second (i.e. operative) configuration wherein the distal portions of the wire members form a helical basket 16 having an open proximal mouth or rim 17, as shown in FIG. 2B. When in such operative configuration (FIG. 2B), the helical basket 16 is sufficiently porous to allow blood to flow therethrough, but sufficiently dense to engage and withdraw in the proximal direction, a thromboembolism. A nose cone 30 is positioned on the distal ends of the wire members 18. The proximal portions 18 of the elongate wire members 20 act as connecting members between the helical basket 16 and the catheter 11. These proximal portions 18 of the wire members 20 are of sufficiently small diameter or are otherwise configured to be retracted through a thromboembolism, without causing substantial disruption or segmentation of the thromboembolism. In some embodiments energy (e.g. heat, vibration, etc.) may be applied to the proximal portions 18 of the wire members 20 to facilitate their retraction through the thromboembolic material without causing substantial disruption or segmentation of the thromboembolism.

The wire members 20 of which the capturing receptacle 14 is formed may be of any suitable material, such as elastic, superelastic or shape memory alloy wire. The distal portions of these wire members are preformed to the shape of the helical basket 16 but are sufficiently elastic to assume substantially straight configurations when retracted through the guide bores 26 and into the catheter 11 and maintained in a taut state under a small amount of proximally directed pressure. (See FIG. 2A) However, when these preformed wire members are extended or advanced through the guide bores 26 and out of the distal end DE of the catheter 11, and relieved of the surrounding restraint of the catheter 11 and the proximally-directed tension, they will resiliently self-coil into the generally frustoconical shape of the helical basket 16.

To facilitate the desired advancement and retraction of these preformed wire members 20, the proximal ends of these members 20 are attached to the distal end of a longitudinally slidable actuator 24 which is positioned within the lumen 22 of the catheter body 12. A hollow actuator lumen 22a extends through the actuator 24 and is in axial alignment with the lumen 22 of the catheter body 12. The shaft of the actuator 24 has a wire braid 25 formed therein to impart stiffness and strength. A distal tip member 28 is formed on the distal end DE of the catheter body 12, such distal tip member 28 having a hollow tip member lumen 22TM which extends longitudinally through the center thereof, and four (4) wire passage bores 26 which also extending longitudinally therethrough, at radially spaced-apart locations (i.e., the 3, 6, 9 and 12 o'clock positions). The distal tip member 28 may be formed of material which is more rigid than the catheter body 12 and may have a proximal portion 40 of reduced diameter which is inserted into the distal end DE of the catheter body lumen 22, as shown in FIGS. 2A, 2B and 2D. Each of the four (4) preformed segments 20 which form the obstructive matter capturing receptacle 14, when advanced out of the catheter 11 must pass through a respective one of the wire passage bores 26 formed in the catheter tip member 28. FIG. 2D' shows an alternative construction of the distal tip member wherein four (4) cut-out notches 26alt are formed at the 3, 6, 9 and 12 o'clock positions to serve as discrete guide wire passageways for the individual wire segments 20, in lieu of the wire passage bores 26.

As seen in FIG. 1, a proximal actuator shaft 24' attached to the actuator 24 extends to a housing 13 formed on the proximal end of the catheter. The proximal actuator shaft 24' may be manually advanced and retracted to control deployment and retraction of the obstructive matter capturing receptacle 14. A contrast medium injection port 15 is also formed on the proximal housing 13, for injection of radiographic contrast medium through the lumen 22 and out of the distal end DE of the catheter 11. In this regard, it is preferable that the outer diameter of the guidewire GW be at least slightly less than the inner diameter of the lumen 22 to permit some radiographic contrast medium to pass through the lumen 22 and out of the distal end of the catheter even when the guidewire is positioned within the lumen. Also, radiographic contrast solutions (i.e., dyes) of minimal viscosity may be selected to enhance the ability of the contrast medium to pass through the lumen 22 while the guidewire GW is positioned therewithin.

When the actuator 24 is withdrawn in the proximal direction, it will pull the wire segments 20 in the proximal direction, through the wire passage bores 26 and into the lumen 22 of the catheter. When the actuator 24 is fully retracted, as shown in FIG. 2A, the segments 20 will be drawn fully through the wire passage bores 26 and will assume substantially straight configurations, and the nose cone 30 mounted on the distal end of the obstructive matter capturing receptacle will be in direct abutment with the catheter tip member 28 such that the hollow nose cone lumen 22NC is in axial alignment with the distal tip lumen 22DT and the lumen 22 of the catheter body 12.

Second Embodiment

FIGS. 3B and 3B' show a second embodiment of an over-the-wire catheter device 10' which differs from the first embodiment 10 in several ways. For example, the obstructive matter-capturing receptacle (not shown) of this second embodiment is formed by only two (2) wire members 20' instead of four (4) as in the first embodiment 10. Also, the catheter 11' of this second embodiment incorporates an elongate distal segment 270 of reduced diameter and increased flexibility—similar to that of the commercially available microcatheters (e.g., Prowler™ microcatheter, Cordis Endovascular Systems, Miami Lakes, Fla.), an example of which is shown in FIG. 3A and generally comprises a proximal portion PP having a lumen L and a distal segment 270 having a lumen 271 which is continuous with the lumen L of the proximal portion PP.

With specific reference to FIGS. 3B and 3B', this second embodiment of the over the wire embolectomy catheter device 10' comprises an elongate, pliable catheter 11' having a helical basket type obstructive matter capturing receptacle (not shown) similar to that of the first embodiment, but wherein the receptacle (not shown) is formed of only two (2) wire members. As in the above described first embodiment, the obstructive matter capturing receptacle (not shown) of this second embodiment 10' is initially retractable to a first (i.e., stowed) configuration and is subsequently advanceable to second (i.e. operative) configuration which is essentially the same as that described above with respect to the first embodiment 10.

In this second embodiment, the flexible catheter 11' comprises a proximal portion 12' having a first diameter and first flexibility, and a distal portion 270 which has a second (i.e., smaller) diameter and a second (i.e., greater) flexibility. An insert member 28' having four (4) guide bores 26' extending longitudinally therethrough, is positioned within the lumen 271' of, and is coextensive with, the distal portion 270 of the catheter 11'. This insert member 28' is a generally cylindrical member having four (4) longitudinal bores 20' extending therethrough, as shown in FIG. 3B'. However, since the obstructive matter capturing receptacle (not shown) of this embodiment is formed of only two (2) elongate members 20', the remaining two guide bores 26' remain unoccupied and may serve as passageways through which radiographic contrast medium (e.g., dye), medicaments, perfusion solution or other fluid my flow.

B. Rapid Exchange Embodiments of the Embolectomy Catheter Device

FIGS. 3D, 3D', 3E, 3E', 3F', 3F' and 4 are illustrative of rapid exchange embodiments of the embolectomy catheter device 10", 10''' and 10''''. These rapid exchange embolectomy catheter devices 10', 10''' and 10'''' incorporate guidewire lumens which extend through only a distal portion of the catheter 11", 11''', 11'''' so as to permit the catheter 11", 11''', 11'''' to be exchanged without the need for use of an exchange-length guidewire (i.e., a guidewire which is long enough to allow the exteriorized portion of the guidewire to be longer than the catheter so that the catheter may be withdrawn, removed and exchanged while holding the guidewire in substantially fixed position. These rapid-exchange embodiments are particularly suited for the treatment of stroke by removing thromboemboli from small blood vessels of the brain (i.e., blood vessels located on, in or around the brain), as the use of exchange-length guidewires may be undesirable in such delicate neuroradiological procedures. see, Morris, P., *Practical Neuroradiology*, Chapter 2, page 41 (Williams & Wilkins 1997)

Third Embodiment

FIGS. 3D and 3D' show a third embodiment (i.e., a rapid exchange type embodiment) of the embolectomy catheter device 10" which is similar in construction to the above described second embodiment 10', but which incorporates a guidewire passage port 267' formed in the sidewall of the catheter 11" near the distal end of its proximal portion 12', and a guidewire deflector tube 260' which extends from the guidewire passage port 267' to the lumen 22'. The guidewire deflector tube 260' has a flared distal end which is held in a centered position within the lumen by a plurality of radial support members 264'. Longitudinal passages 266,266(alt) are formed between the radial support members 264' to allow radiographic contrast medium or other fluid to flow through the lumen 22', past the flared distal end of the guidewire deflector tube 260'. Selected ones of the longitudinal passages 266(alt) are larger than the others 266 to permit the elongate members 20' which form the obstructive matter capturing receptacle to pass therethrough, as shown. The proximal end of a guidewire PEG may be inserted into the distal end opening DEO of the catheter 11" and, thereafter, the catheter 11" may be advanced in the distal direction such that the proximal end of the guidewire PEG will enter the flared distal end of the guidewire deflector tube 260', and will be thereby deflected out of the side guidewire passage port 267', as shown.

Fourth Embodiment

In the fourth embodiment (i.e., another rapid exchange embodiment) shown in FIGS. 3E and 3E', the catheter 11''' comprises a main tube 300 which has a proximal portion 302 of a first diameter D1 and a distal portion 304 of a second diameter D2. A side tube 308 is affixed to one side of the distal portion 304 of the main tube 300, and a guidewire passage aperture 310 is formed into the lumen 309 of the side tube 308, such that the lumen 309 of the side tube may be used as the guidewire lumen, and the distal portion of the guidewire GW which emerges from the side tube lumen 309 may then be passed through the separate guidewire lumen of the obstructive matter capturing receptacle 22 (not shown in FIG. 3E) and/or any nose cone lumen 22NC (not shown in FIG. 3E), as described fully hereabove.

Fifth Embodiment

The fifth embodiment (i.e., another rapid exchange embodiment) of the embolectomy catheter device 10'''' is similar in construction and operates in the same manner as the fourth embodiment 10''' described above, except that the main tube 300' of this fifth embodiment 10'''' is formed of a continuous wire 316 which is would in a tight helical coil, as shown. This construction of the main tube 300' may provide enhanced flexibility over other forms of construction.

C. Alternative Components and Optional Elements which May be Incorporated into any Embodiment of the Embolectomy Catheter Devices I. Alternative Types of Obstructive Matter Capturing Receptacles:

The embolectomy catheter devices 10, 10', 10", 10''', 10'''' of the present invention may incorporate various types of obstructive matter capturing receptacles as alternatives to the helical wire basket type receptacles 14, 14' shown in FIGS. 1A, 2B and 4. In particular, several alternative obstructive matter capturing receptacles are shown in FIGS. 5-7.

FIGS. 5-5A show one alternative obstructive matter-capturing receptacle 400 which comprises a plurality of elastic or superelastic wire spokes 402 which are preformed to a radially splayed configuration as shown, and which have a membranous or fabric cover 404 disposed thereon to form an umbrella like structure. The membranous or fabric cover 404 may be of non-porous or porous configuration, and is preferably formed of material such as polyethylene, polytetrafluoroethylene, polyurethane, ethylene vinyl acetate or silicone. A central hub is formed at the center of the spokes 402, and a guidewire lumen extends through such central hub such that the guidewire may pass the center of the receptacle 400, in the manner depicted in FIGS. 5 and 5A. The ends of the spokes 402 may have bulbs 408 formed thereon to minimize trauma to the surrounding blood vessel walls, as shown in FIG. 5'. Or, as an alternative to such bulbs 408, atraumatic loops 410 may be formed on the distal ends of the spokes 402 to prevent vascular trauma. The spokes 402 are of sufficiently small diameter to be retracted through a thromboembolism without causing substantial disruption of segmentation of the thromboembolism.

FIGS. 5B-5B" show another obstructive matter capturing receptacle 420 which comprises a plurality of elastic or superelastic wire spokes 402' which are pre-formed to a radially splayed configuration as shown, and a porous fabric (e.g., woven, knitted, mesh or net fabric) sac 422 attached to the spokes 402' to form an umbrella-like structure, as shown. The material used to form this sac 422 may be the same microporous material as specified hereabove with respect to the membranous or fabric cover 404 of the embodiment shown in FIG. 5. A central aperture 426 is formed in the sac 422 such that a guidewire GW may be passed through a region among the spokes 402', and through such aperture 426, as shown in FIGS. 5B and 5B'. Draw lines 424 are attached to the free ends of the spokes 402' and extend through the lumen of the catheter. These draw lines 424 and the spokes 402' are of sufficiently small diameter to be retracted through a thromboembolism without causing substantial disruption or segmentation of the thromboembolism. After the receptacle 420 has been advanced through the thromboembolism, it is deployed (e.g., radially expanded) and retracted such that the draw lines 424 and spokes 402' will retract through and will become located proximal to, the thromboembolism. Thereafter, the draw lines 424 are retractable into the catheter to pull distal ends of the spokes 402' inwardly such that the proximal mouth PM of the sac will be drawn partially around the captured obstructive matter in the manner shown in FIGS. 5B' and 5B".

FIG. 5C shows another alternative obstructive matter capturing receptacle which employs a resilient, generally football shaped cage to effect radial expansion/contraction of a membranous or fabric cover 444. As shown, the cage comprises approximately six (6) elongate members 442 of preformed elastic, super-elastic or shape memory metal wire disposed longitudinally about a longitudinal axis LA, and having the membranous or fabric covering 444 disposed on the distal portions DP thereof. The distal ends DE of the elongate members 442 are attached to a nose cone 446 which has a guidewire passage lumen extending longitudinally therethrough. When retracted into the lumen of the catheter, the members 442 will radially compress to a diameter which is received within the catheter lumen. However, when advanced out of the catheter the members 442 will resiliently expand to the configuration shown. The proximal portions of the members are sufficiently small in diameter to slice, cut or otherwise pass in the proximal direction through a thromboembolism or clot without disrupting or causing fragmentation of the thromboembolism or clot.

FIGS. 7 and 7A show an alternative helical basket type of obstructive matter capturing receptacle 14" which is of the same general configuration, and operates in the same manner, as the helical basket type receptacles 14, 14' shown in FIGS. 1A and 4, but wherein the receptacle 14" is formed of a plurality of flat ribbons 500 formed of metal such as Elgiloy™ cobalt-chromium-nickel alloy (Elgiloy, Inc., Elgin, Ill.) or suitable resilient plastic. The distal portions of the flat ribbons 500 are preformed to helical configurations to form the helical basket 502. The proximal portions of the ribbons 500 serve as connector members 504 between the helical basket 502 and the catheter 11. Each ribbon 500 has first and second flat surfaces 512 and first and second edges 514. Each of the ribbons 500 is twisted 90 degrees at a point of transition 510 between the connector members 504 and the helical basket 502. This twisting of the ribbons causes a) the distal portions to be situated with their edges 514 in juxtaposition such that a thromboembolus contained within the helical basket 502 will rest upon the flat surfaces of the ribbons 500, and b) the proximal portions to be situated with their edges aimed in the proximal direction to facilitate retraction of the distal connector members 504 through the thromboembolus without causing the thromboembolus to be substantially fragmented or disrupted.

Optional Guide Catheter/Proximal Obstructive Matter Retaining Member:

As illustrated in FIG. 6, it may be desirable to use the embolectomy catheter devices 10, 10', 10", 10''', 10'''' in conjunction with a guide catheter 50 through which the embolectomy catheter 11 may be advanced. When such guide catheter 50 is used, a proximal obstructive matter retaining member 52, such as a tubular sheath having a radially flared and splayable distal end as shown in FIG. 5A, may be advanced out of the distal end DE of the guide catheter 50 such that the clot C or other obstructive matter may be captured between the distal obstructive matter receiving portion 16 of the receptacle 14 and the flared distal end of the proximal obstructive matter retaining member 52. The use of this optional proximal obstructive matter retaining member 52 may be particularly useful in cases where the thromboembolism is very fresh or has been inadvertently severed or segmented so as to present a danger of breaking apart or fragmenting during the removal procedure.

D. Rapid Exchange Microcatheter Useable in Conjunction with the Embolectomy Catheters In many procedures wherein the embolectomy catheters of this invention are used to remove thromboemboli from small blood vessels of the brain, it will be desirable to initially perform an angiogram of the blood vessel wherein the thromboembolism is believed to be located to a) verify the exact location of the thromboembolism and b) radiographically map the vascular anatomy in the immediate area of the thromboembolism and c) guide and verify the passage of a small guidewire through the offending thromboembolism. Because the embolectomy catheters 10, 10', 10", 10''', 10'''' of the present invention may necessarily be of very small diameter (e.g., 0.10-0.20 inches) in order to navigate the tiny blood vessels of the brain, the presence of the retracted obstructive matter capturing receptacle 14, 14', 400, 420 or 440 within that catheter 11 may severely limit the amount of radiographic contrast medium which could be infused though that catheter 11. Thus, in many instances, it may be desirable to initially insert a small angiography catheter (e.g., a microcatheter such as the Prowler™ microcatheter, Cordis Endovascular Systems, Miami Lakes, Fla.), an example of which is shown in FIG. 3A, into the obstructed blood vessel to perform the initial angiography and to accomplish precise positioning of the guidewire through the thromboembolism. After the initial angiography has been performed and the guidewire has been precisely positioned, the angiography catheter is withdrawn and removed, leaving the guidewire in place. Thereafter, an embolectomy catheter 10, 10', 10", 10''', 10'''' of the present invention is advanced over the pre-positioned guidewire to the location of the thromboembolism.

However, the microcatheters of the prior art have not been suitably designed for this novel procedure. Such microcatheters have heretofore of an "over-the-wire" type used primarily in procedures where the catheter is retracted and removed concurrently with the guidewire over which it was inserted. Thus, as those skilled in the art will appreciate, the prior art "over-the-wire" type microcatheters can only be exchanged over a stationary guidewire if the guidewire is an "exchange-length" wire or if an extension has been attached to the proximal end of the guidewire to permit the exchange. However, the use of such "exchange-length" guidewire or a guidewire extension may be contraindicated in procedures where the catheters are being inserted into and withdrawn from tiny delicate vessels of the brain. see, Morris, P., *Practical Neuroradiology*, Chapter 2, page 41 (Williams & Wilkins 1997)

In view of this shortcoming of the prior art microcatheters, applicant has devised the rapid-exchange microcatheter 265 shown in FIGS. 3C and 3C'. This rapid exchange microcatheter 265 comprises an elongate, flexible catheter having a proximal portion 12" of a first diameter and first flexibility, and a distal portion 270" which has a second (i.e., smaller) diameter and a second (i.e., greater) flexibility.

A guidewire passage port 267 is formed in the sidewall of the catheter near the distal end of its proximal portion 12", and a guidewire deflector tube 260 extends from the guidewire passage port 267 to the lumen 271. The guidewire deflector tube 260 has a flared distal end which is held in a centered position within the lumen by a plurality of radial support members 264. Longitudinal passages 266 are formed between the radial support members 264 to allow radiographic contrast medium or other fluid to flow through the lumen 271, past the flared distal end of the guidewire deflector tube 260. The proximal end of a guidewire PEG may be inserted into the distal end opening DEO of the catheter and, thereafter, the catheter may be advanced in the distal direction such that the proximal end of the guidewire PEG will enter the flared distal end of the guidewire deflector tube 260, and will be thereby deflected out of the side guidewire passage port 267, as shown in FIG. 3C.

E. Methods for Using the Invention to Remove Clots or Other Obstructive Matter from Blood Vessels FIGS. 8A-8F illustrate an exemplary method of using an the over-the-wire type embolectomy catheter 10 of the invention to remove a obstructive matter such as a thromboembolism or blood clot, while FIGS. 9A-9C illustrate an exemplary method of using a rapid exchange type embolectomy catheter 10" of the invention to remove such obstructive matter. These exemplary procedures are described in detail in the paragraphs below.

Exemplary Use of the Over-The-Wire Embolectomy Catheter

FIGS. 8A-8F show an exemplary method for using the over-the-wire type embolectomy catheter 10 shown in FIGS. 1-2D to remove a thromboembolus or clot C which has become lodged immediately downstream of an arterial bifurcation BE so as to create an ischemic zone IZ of tissue (e.g., brain tissue which is deprived of oxygen and other nutrients) located downstream of the clot C. The exemplary procedures depicted in these drawings are described in the paragraphs herebelow.

Initially, a microcatheter such as the rapid exchange microcatheter 265 of FIG. 3C (not shown in FIGS. 8A-8F) is advanced to a position near the obstructive matter or clot C and radiographic contrast medium is injected through the microcatheter to angiographically verify the precise location of the clot C and to visualize or map the anatomy of the blood vessels in the area of the clot. Thereafter, a guidewire having a diameter of 0.01-0.014 inches and a length which is not more than 1.5 times the length of the microcatheter 265 (i.e., not an "exchange-length" guidewire) is advanced from the lumen 271 of the microcatheter 265 until its distal tip DT has passed through the clot C as shown in FIG. 8A.

Thereafter, the operator will hold the proximal end of the guidewire GW to prevent longitudinal retraction of the guidewire GW while retracting and removing the rapid exchange microcatheter 265. This allows the guidewire GW to remain in its operative position as shown in FIG. 8A.

Figure 8B:
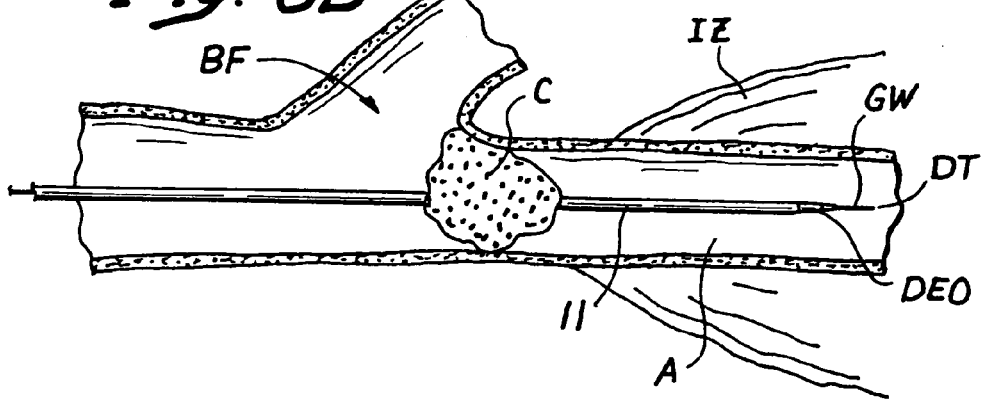
Figure 9A:
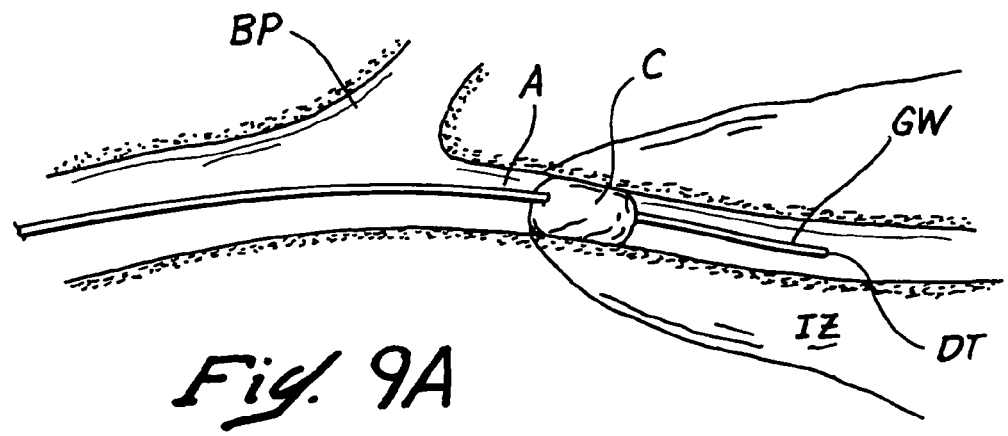
FIGS. 9A-9D are step-wise showings of a procedure wherein the third embodiment (i.e., a rapid exchange embodiment) of an embolectomy catheter of the present invention is used to remove a blood clot from a small blood vessel of a mammalian body.
Figure 9B:
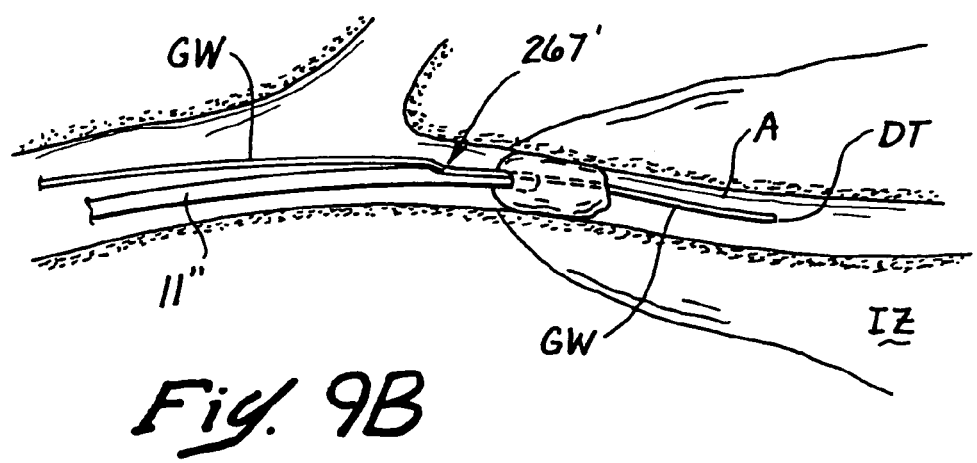
Figure 9C:
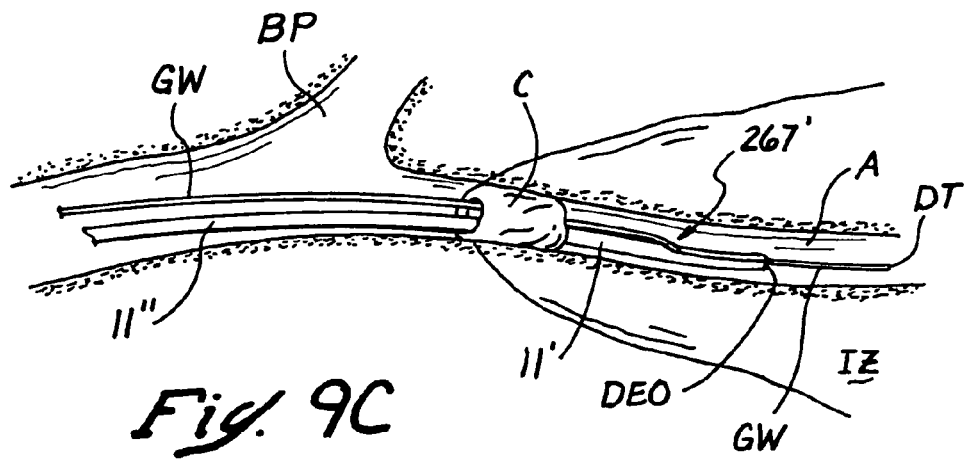

Thereafter, as shown in FIG. 8B, the embolectomy catheter 11 having its obstructive matter capturing receptacle retracted to its first configuration (FIG. 2A) is advanced over the guidewire GW and through the clot C, such that the distal end opening DEO of the catheter 11 is located downstream of the clot C but still proximal to (i.e., upstream of) the distal tip DT of the guidewire GW.

Figure 8C:
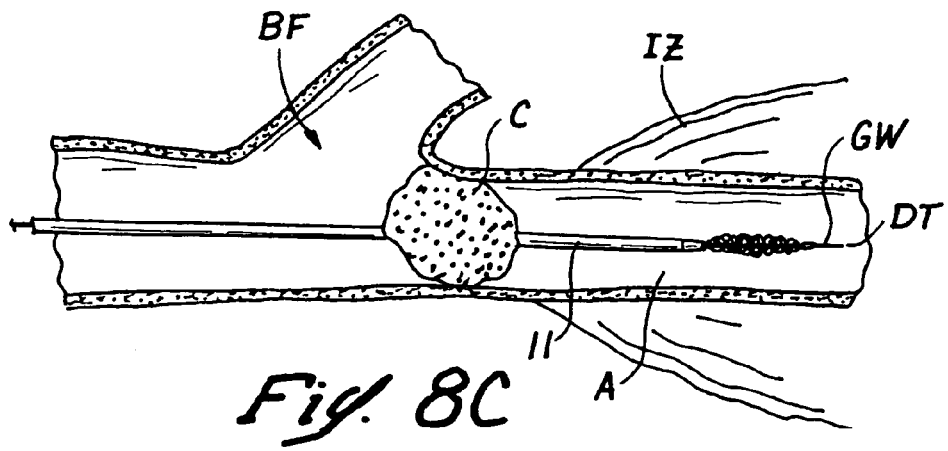
Figure 8D:
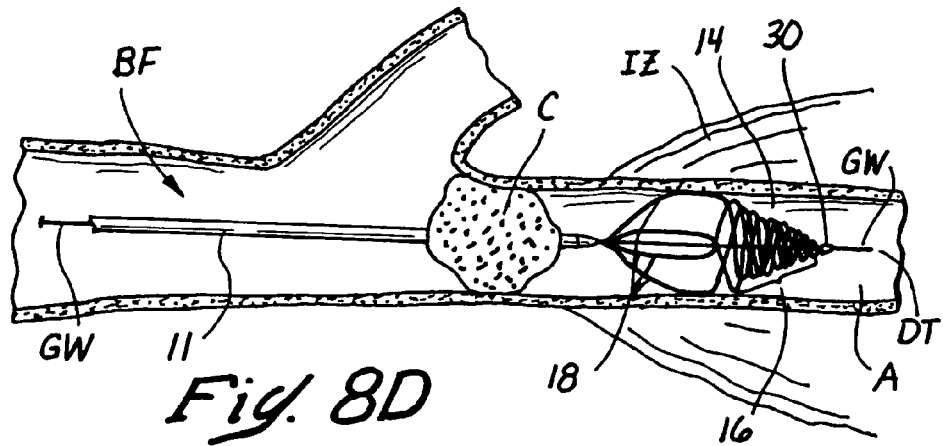

Thereafter, as shown in FIGS. 8C and 8*d*, the actuator 28 is advanced in the distal direction to cause the four wire segments 20 which form the obstructive matter capturing receptacle 14 to advance out of the distal end of the catheter such that the nose cone 30 remains upon the guidewire GW. In this manner, the obstructive matter capturing receptacle 14 is fully deployed to its second or operative configuration at a location distal to (i.e., downstream of) the clot C (FIG. 3D).

Figure 8E:
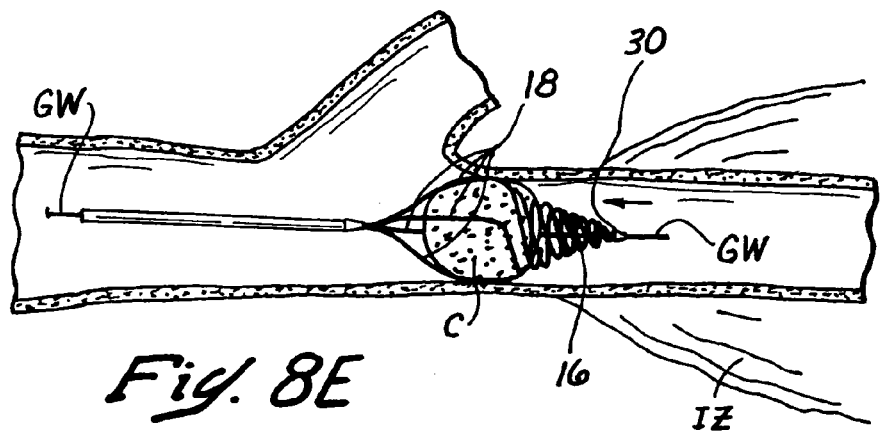

Thereafter, as shown in FIG. 8E, the embolectomy catheter 11 is retracted in the proximal direction to cause the proximal connector members 18 of the obstructive matter capturing receptacle 14 to pass through the clot, and to further cause the clot to be received within the concave or cavernous interior of the distal obstructive matter receiving portion 16 of the receptacle 14, as shown.

Figure 8F:
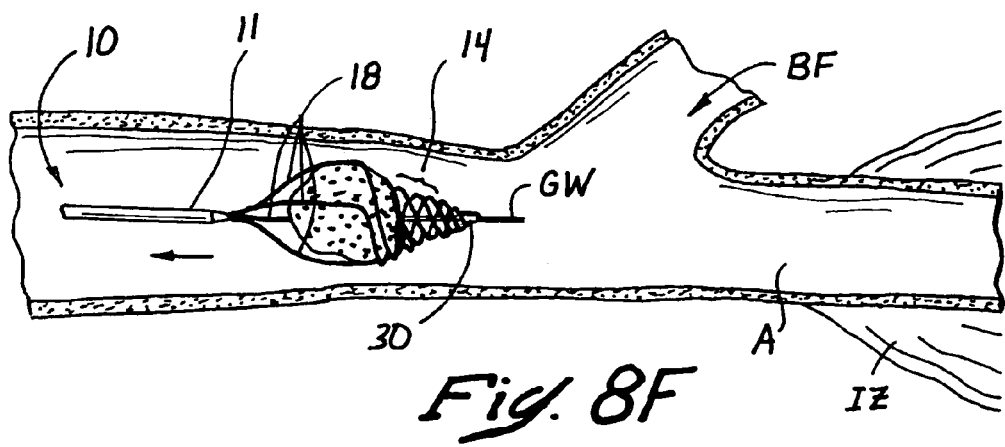

Thereafter, as shown in FIG. 8F, the entire embolectomy catheter device 10, with the clot C in tow, may be retracted out of the body—or to a location within a larger blood vessel (e.g., a jugular vein or the vena cave) where the clot C and the fully deployed obstructive matter capturing receptacle 14 may be received within the lumen of a larger catheter to further secure the clot for ultimate extraction and removal form the body.

Exemplary Use of the Rapid Exchange Embolectomy Catheter

The exemplary method of using a rapid exchange type embolectomy catheter of this invention 10" is shown in FIGS. 9A-9D.

Initially, a microcatheter such as the rapid exchange microcatheter 265 of FIG. 3C (not shown in FIGS. 9A-9D) is advanced to a position near the clot C and radiographic contrast medium is injected through the microcatheter to angiographically verify the precise location of the clot C and to visualize or map the anatomy of the blood vessels in the area of the clot. Thereafter, a guidewire having a diameter of 0.006-0.018 inches and a length which is not more than 1.5 times the length of the microcatheter 265 (i.e., not an "exchange-length" guidewire) is advanced from the lumen 271 of the microcatheter 265 until its distal tip DT has passed through the clot C as shown in FIG. 9A.

Thereafter, the operator will hold the proximal end of the guidewire GW to prevent longitudinal retraction of the guidewire GW while retracting and removing the rapid exchange microcatheter 265. This allows the guidewire GW to remain in its operative position as shown in FIG. 9A.

Thereafter, as shown in FIG. 9B, the exteriorized proximal end of the guidewire is inserted into the distal end opening DEO of the rapid exchange embolectomy catheter 11" while its obstructive matter capturing receptacle is retracted to its first configuration (FIG. 2A) within the distal portion of the catheter 11". As the catheter is advanced in the distal direction over the guidewire GW, the guidewire will be deflected by the guidewire deflection tube 260' (see FIG. 3D) and the proximal end of the guidewire will emerge out of the side guidewire passage aperture 267' of the catheter 11". The catheter 11" is advanced through the clot C, such that the distal end opening DEO of the catheter 11" is located downstream of the clot C but still proximal to (i.e., upstream of) the distal tip DT of the guidewire GW, as shown in FIG. 9C. The guidewire GW extends along side of the proximal portion of the rapid exchange catheter 11" (i.e., the portion of the catheter proximal to the guidewire passage aperture 267'), as shown.

Figure 9D:
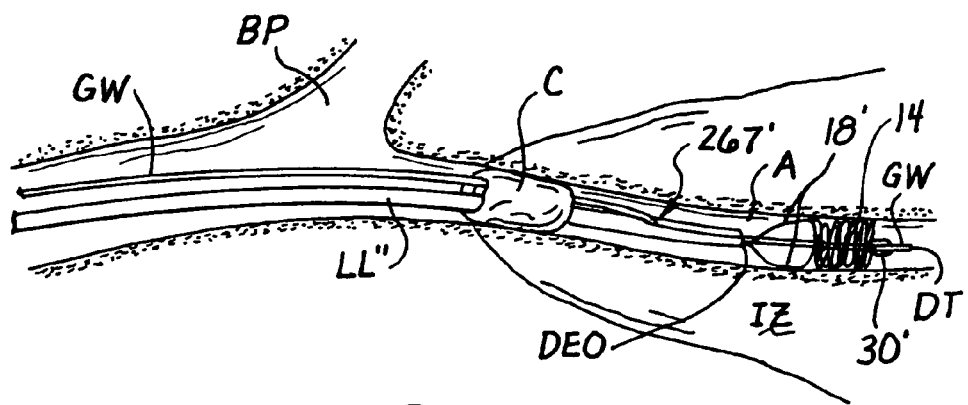

Thereafter, as shown in FIG. 9D, the actuator 28 is advanced in the distal direction to cause the two (2) wire members 20' which form the obstructive matter capturing receptacle 14' to advance out of the distal end of the catheter 11' such that the nose cone 30' remains upon the guidewire GW. In this manner, the obstructive matter capturing receptacle 14' is fully deployed to its second or operative configuration at a location distal to (i.e., downstream of) the clot C (FIG. 9D).

Thereafter, the rapid exchange embolectomy catheter 11' is retracted in the proximal direction to cause the proximal connector members 18' of the obstructive matter capturing receptacle 14' to pass through the clot, and to further cause the clot to be received within the concave or cavernous interior of the helical basket 16' of the receptacle 14'. The clot C is then removed by retraction of the catheter 11', in the same manner shown and described above and shown in FIGS. 8E and 8F.

Exemplary Embolectomy Catheter

Figure 10:
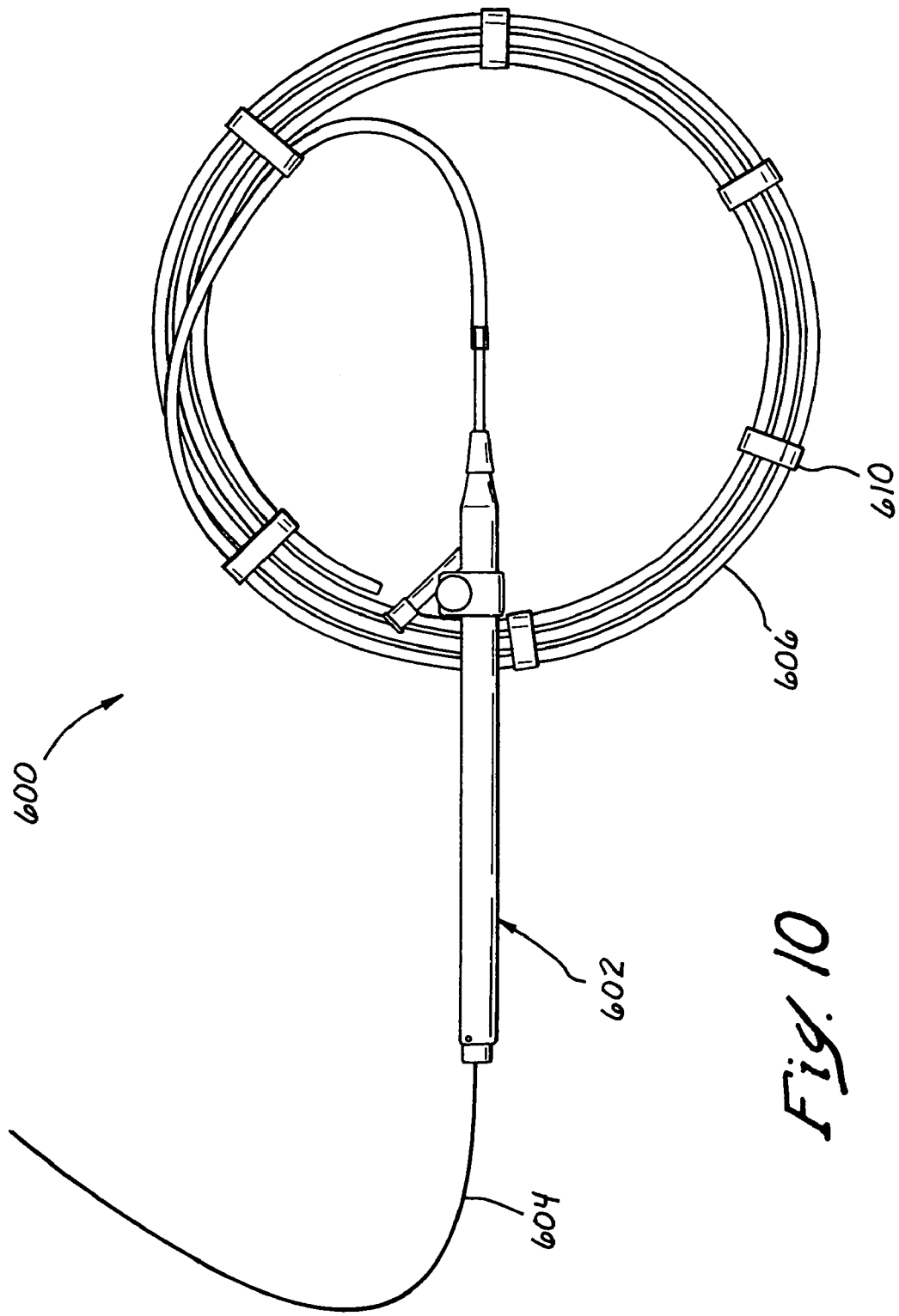
FIG. 10 is elevational view of an exemplary embodiment of an over-the-guidewire and embolectomy catheter of the present invention including an exemplary operating handle and coiled storage configuration.

FIGS. 10-19 illustrate various aspects of an exemplary "over-the-wire" embolectomy catheter 600 of the present invention that utilizes a nested wire type of clot capture device. The embolectomy catheter 600 is seen in FIG. 10 in its entirety, and as it would appear in its shipping package. The embolectomy catheter 600 comprises an operating handle 602, a guidewire 604, and an insertion portion (608 in FIG. 11A) that is hidden by a storage coil 606. The storage coil 606 comprises a flexible length of tubing to protect the insertion portion 608, and is held in its coiled configuration by a plurality of brackets 610.

FIG. 11A illustrates the embolectomy catheter 600 removed from the storage coil 606 of FIG. 10. The insertion portion 608 is shown on the right, or distal side, in broken line to enable visualization of its entire length. More specifically, the insertion portion 608 has a length $L_c$ from the handle 60 to a distal end 611 of approximately 59 inches to enable access to distant reaches of a patient's vasculature through an access incision in the femoral artery, for example.

The operating handle 602 includes a rigid handle body 612 having a proximal end 614 and a tapered distal end 616. An elongate channel 618 opening upward as seen in FIG. 11A extends substantially the entire length of the handle body 612. Throughbores on either end of the channel 618 provide passages for elements of the embolectomy catheter 600. In particular, a throughbore on the proximal end 614 receives a guidewire introducer 620 having a tapered configuration. A bore 621 of the guidewire introducer 620 sealingly mates with an inner hypotube 622 as indicated at 624. The hypotube 622 continues in a distal direction to mate with an inner tube of the insertion portion 608, as will be more fully described below. A strain relief nose 626 and a strain relief tube 628 are fastened to the tapered distal end 616 of handle body 612. These two strain relief elements 626, 628 prevent damage to the insertion portion 608 from excessive bending as it passes out of the through bore in the distal end 616.

With reference now to FIGS. 11A-11C, a sliding infusion port 630 is mounted for linear translation within the channel 618. The sliding infusion port 630, as seen in FIG. 11B, includes a slide portion 632 having a width $w_s$, and a height $h_s$ so as to closely fit within the channel 618. In an exemplary embodiment, the height $h_s$ is slightly greater than the width $w_s$; for example, the height $h_s$ may be about 0.25 inches and the width $w_s$ may be about 0.24 inches. In the same example, the slide portion 632 has a length $l_s$ of about 1.08 inches. A through bore 634 extends from one end of the slide portion 632 to the other. A side tube 636 projects upward at an angle of about 30 degrees from the slide portion 632, and is supported by a web 638. The side tube 636 terminates in an infusion port 640, and a side lumen 642 defined therewithin intercepts the through bore 634 near the distal end of the slide portion 632. A circular shaft journal 644 is provided in the web 638. As will be explained more fully below, the sliding infusion port 630 is fixedly mounted with respect to an outer tube of the insertion portion 608 and causes the outer tube to translate with respect to an inner tube.

With reference again to FIG. 11A, a mechanism for regulating motion of the sliding infusion port 630 includes a thumb-wheel tightening bolt 646 mounted for rotation within the shaft journal 644, and a carriage 648. The carriage 648 surrounds the handle body 612 and maintains the sliding infusion port 630 within the channel 618. Although not shown in detail, the thumb-wheel tightening bolt 646 is configured to clamp the slide infusion port 630 with respect to the handle body 612 to prevent movement therebetween. In this manner, the thumb-wheel tightening bolt 646 is first loosened and then the sliding infusion port 630 is manually slid along the channel 618. The thumb-wheel tightening bolt 646 is useful to maintain the catheter iun an undeployed configuration during packaging and shipment. At the desired position, the thumb-wheel tightening bolt 646 may be tightened to lock the slide infusion port 630 in place. Alternatively, the thumb-wheel tightening bolt 646 may be configured to actually move the sliding infusion port 630 and carriage 648 linearly along the handle body 612. For example, the actuating wheel 646 could have gear teeth that mesh with teeth on a rack provided on the handle body 612. Alternatively, the thumb-wheel tightening bolt 646 may have an elastomeric sleeve made of a material with a high coefficient of friction that frictionally engages a surface of the handle body 612. Whatever the interface between the thumb-wheel tightening bolt 646 and handle body 612, those of skill in the art will understand that a variety of mechanisms can be provided for displacing the sliding infusion port 630 within the channel 618 and fastening it at various locations.

Figure 12:
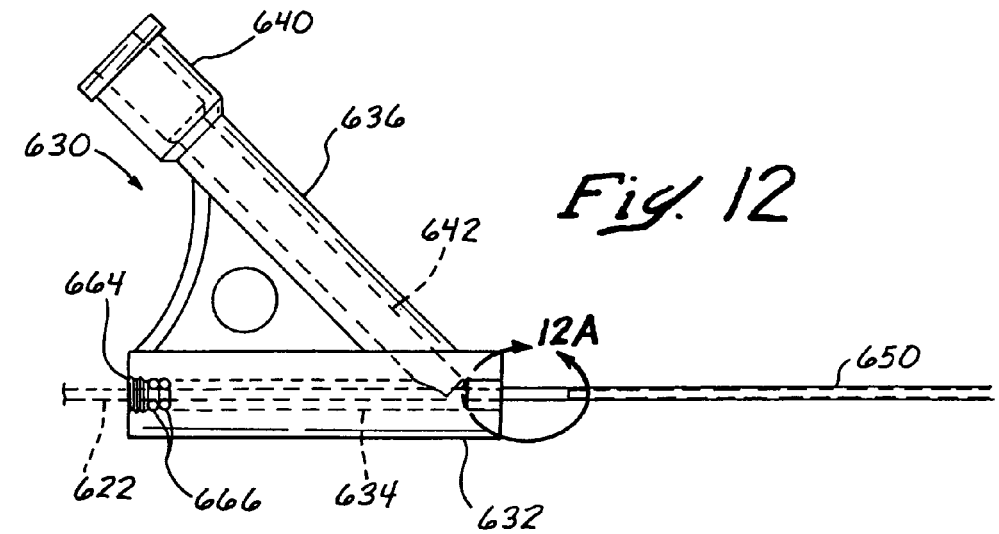
FIG. 12 is an isolated view of the sliding infusion port with an outer tube of the embolectomy catheter attached to the distal end.
Figure 12A:
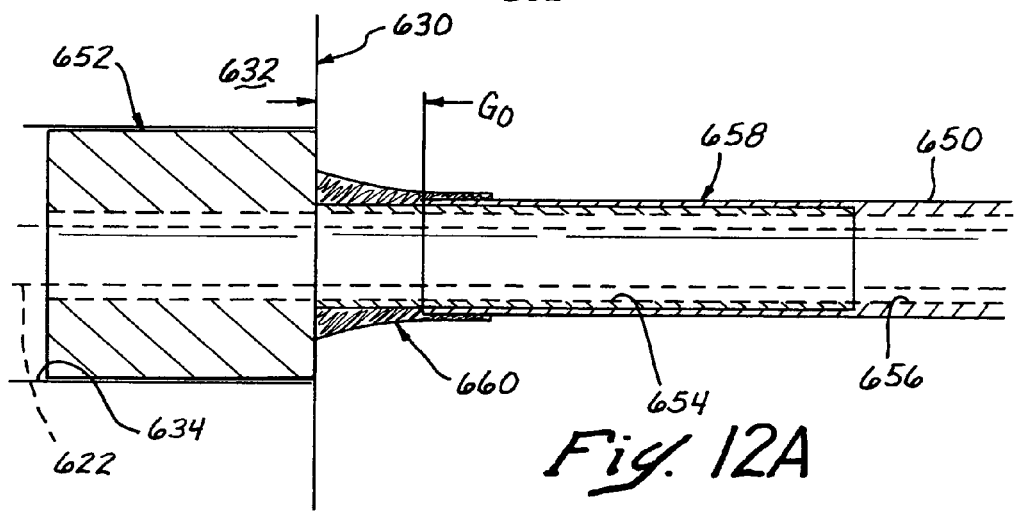
FIG. 12A is a detailed view of the junction between the sliding infusion port and the catheter outer tube.

FIGS. 12 and 12A-12C illustrate the sliding infusion port 630 in greater detail with additional components connected thereto. More specifically, a catheter outer tube 650 attaches to and projects distally from a distal end of the slide portion 632. A detail of the interface between the slide portion 632 and the catheter outer tube 650 is seen in FIG. 12A. A rigid, preferably metal, tubular sleeve 652 is fastened at the distal end of the through bore 634, and has an outer hypotube 654 extending distally therefrom. The catheter outer tube 650 has a lumen 656 that is flared or stepped slightly larger in size at a proximal end to overlap the outer hypotube 654 in the region 658. The catheter outer tube 650 terminates short of the slide portion 632 by a gap $G_o$ which is, at most, 0.1 inches. An adhesive or other suitable bonding compound 660 is provided in this gap $G_o$, and in the annular space between the hypotube 654 and catheter outer tube 650. The sleeve 652 includes a lumen 662 that is sized the same as the lumen of the hypotube 654, and the lumen 656 of the catheter outer tube 650. Consequently, and as will be clear from the description below, the inner hypotube 622 (shown in phantom) passes easily through these co-linear lumens without fictional interference from steps or other such narrowing.

Figure 12B:
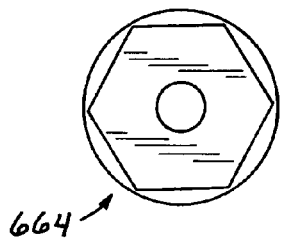
FIG. 12B is an end view of a threaded plug that inserts into the proximal end of the sliding infusion port.
Figure 12C:
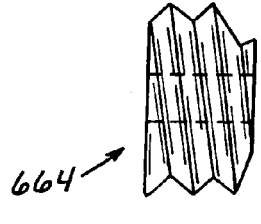
FIG. 12C is a side view of the threaded plug of FIG. 12B.

FIGS. 12B and 12C illustrate a threaded plug 664 that fits within a threaded distal portion of the throughbore 634. The threaded plug 664 holds a pair of seals 666 within the through bore 634. The seals 666 have bore diameters that provide a sliding seal around the inner hypotube 622. By virtue of the seals 666, fluid introduced through the infusion port 640, the side lumen 642, into the through bore 634 is prevented from passing proximally from the throughbore. Instead, the fluid passes through an annular gap between the sleeve lumen 662 and the inner hypotube 622, and then travels distally through the catheter insertion portion 608.

Now with reference to FIGS. 13 and 14, inner and outer telescoping tubes of the catheter insertion portion 608 will be described. FIG. 13 illustrates the catheter outer tube 650 extending from the strain relief tube 628 to a distal end 670. The outer tube 650 comprises a reinforced proximal segment 672, an un-reinforced middle segment 674, and a distal sheath 676 attached in series at 677 to the un-reinforced segment and extending to the distal end 670. The various lengths of these segments are given as: $L_o$ is the length of the outer tube 650, $L_{op}$ is the length of the proximal segment 672, $L_{om}$ is the length of the middle segment 674, and $L_{od}$ is the length of the distal sheath 676. In an exemplary embodiment, $L_o$ equals about 59 inches, $L_{op}$ equals about 52 inches, $L_{om}$ equals about 5 inches, and $L_{od}$ equals about 2 inches.

The catheter outer tube 650 is constructed with higher strength and lower flexibility at its proximal end, and gradually becomes more flexible and consequently less strong in the distal direction. The proximal segment 672 is desirably made of a polymer reinforced with helically wound wires or other suitable means. For example, the polymer may be polyether block amide, sold under the trade name PEBAX, and the reinforcements may be 16 stainless-steel wires arranged in a helical array. The middle segment 674 is desirably an un-reinforced polymer, such as polyurethane. Finally, the distal sheath 676 is a relatively thin polymer tube, preferably PEBAX.

A portion of a reinforced catheter inner tube 680 is seen in FIG. 14, and includes a proximal reinforced segment 682 and a distal un-reinforced segment 684. Along the insertion portion 608 (FIG. 11A), the length of the reinforced inner tube 680 is approximately equal to the length of the catheter outer tube 650. The length $L_{ip}$ of the proximal reinforced segment 682 may be about 32 inches, while length $L_{id}$ of the distal un-reinforced segment 684 is about 27 inches.

The reinforced catheter inner tube 680 comprises an inner tube 686, a reinforcing sleeve 688 surrounding a proximal segment of the inner tube 686, and a distal segment 690 extending distally from the inner tube at a transition region 692. The inner tube 686 and attached distal segment 690 extend the entire length of the reinforced inner tube 680, while the reinforcing sleeve 688 terminates slightly past the midpoint thereof, closer to the distal end. The reinforcing sleeve 688 is desirably a polymer shrink tube closely fitting around the inner tube 686. As with the catheter outer tube 650, the reinforced inner tube 680 becomes more flexible and less strong moving in the distal direction. The length $L_{i12}$ of the inner tube 686 is desirably between about 55 inches, while the length $L_{i4}$ of the distal segment 690 is desirably between about 1-6 inches, and in a specific embodiment for treating ischemic stroke is about 4 inches.

The inner tube 686 is desirably made of a polymer tube reinforced with helically wound wires, or the like. For example, the inner tube 686 may be a PEBAX tube reinforced with 12 stainless-steel wires. Finally, the distal segment 690 is also preferably reinforced, but to a lesser extent than the inner tube 686. Therefore, the distal segment 690 may be, for example, a tube of PEBAX reinforced with 4 stainless steel wires. This construction is seen in greater detail in FIGS. 16A-16D. It can thus be appreciated that the distal segment 690 may be a continuation of inner tube 686, with some of the reinforcing wires removed. That is, for example, the inner tubes 686 may be reinforced with an array of 12 wires wrapped helically therearound, and the distal segment 690 has only 4 wires wrapped helically therearound resulting from simply removing 8 of the reinforcing wires in the area of the distal segment 690.

With reference now to FIGS. 15 and 15A, the proximal end of the elements making up an inner lumen of the embolectomy catheter 600 is seen. FIG. 15 shows the operating handle body 612 in phantom to better illustrate the interaction between the guidewire introducer 620, the inner hypotube 622, the sliding infusion port 630, and the reinforced inner tube 680, all previously described. The catheter outer tube 650, as detailed in FIGS. 12 and 12A, is removed in FIG. 15 so that a junction between the inner hypotube 622 and the reinforced inner tube 680 can be seen, and further detailed in FIG. 15A.

As mentioned previously, the sliding infusion port 630 can be displaced within the channel 618 in the handle body 612, and rides over the inner hypotube 622. In this regard, the seals 666 held in by the threaded plug 664 maintained a fluid-tight seal between the through bore 634 of the sliding infusion port 630, and inner hypotube 622. Again, this sliding seal ensures that fluid introduced through the infusion port 640 travels in a distal direction between the catheter outer tube 650, and reinforced inner tube 680. Although not shown in FIG. 15, the reader will appreciate that upon displacement of the sliding infusion port 630, the connected catheter outer tube 650 (see FIG. 12) also travels telescopically over the inner hypotube 622, and over the reinforced inner tube 680.

As detailed in FIG. 15A, the inner hypotube 622 connects in series with the reinforced inner tube 680 using a junction sleeve 694 and adhesive 696 or other suitable bonding compound. That is, the inner hypotube 622 exhibits a reduction in diameter at a step 698, which reduction is sufficient to permit the inner hypotube to fit within the inner tube 686 in an overlap region 700. A gap $G_i$ of approximately 0.05 inches is provided between the proximal end of the inner tube 686 and the step 698. The junction sleeve 694 is preferably a shrink tube that fits closely around the inner hypotube 622 just proximal to the step 698, and extends around the proximal end of the reinforcing sleeve 688. It should be noted that the sleeves 688 and 694 are desirably shrink tubes, and the gaps seen in the drawings are only for illustration purposes, and would not be present in the actual catheter 600.

The junction sleeve 694 helps ensure no leakage into or out of a continuous inner lumen 702 formed along the length of the inner hypotube 622 and inner tube 686. In addition, the junction between the inner hypotube 622 and reinforced inner tube 680 is desirably provided within the tapered distal end 616 of the handle body 612, and thus is positioned out of the range of travel of the sliding infusion port 630, which might otherwise catch on one of the tubular edges and interfere with the connection.

The inner lumen 702 continues from the inner hypotube 622, and through the entire reinforced inner tube 680 to the distal end 611 of the insertion portion 608, seen in FIG. 11A. The inner lumen 702 provides a channel for the guidewire 604 (FIG. 10) from the connected guidewire introducer 620 to the distal end of the catheter 600. In addition, the inner lumen 702 provides a passageway for an infusion guidewire of the present invention, as will be detailed below.

FIGS. 16A-16D illustrate various steps in the fabrication of the reinforced inner tube 680. FIG. 16A shows the entire length of the inner tube 686 and distal segment 690. As can be appreciated by one of skill in the art, the entire length seen in FIG. 16A is desirably constructed of a single reinforced tube, wherein some of the reinforcement has been removed along the distal segment 690. In a specific preferred example, the entire length initially has 12 wires in a helical array 704, and the wires have been removed in the distal segment 690 to form a 4-wire helical array 706. Again, as seen in FIG. 14, in a specific embodiment for treating ischemic stroke the length $L_{i4}$ of the distal segment 690 is about 4 inches.

FIG. 16B shows a length $L_{tt}$ of tip tubing 708 fused over the distal segment 690 at a joint 710. The length $L_{tt}$ is desirably about 1.5 inches, and the tip tubing 708 is preferably a flexible polymer, such as PEBAX.

FIG. 16C shows the reinforcing sleeve 688 added to the assembly of FIG. 16B. The total length of the reinforced inner tube 680 plus the tip tubing 708 is given as $L_i$, and is desirably about 65 inches. Therefore, it will be understood that the length of the reinforced inner tube 680 seen in FIG. 14, which added up to about 59 inches, is only that portion projecting distally from the strain relief tube 628 (FIG. 13), and not including the length of the tip tubing 708. Also, as mentioned above, although a gap is seen between the inner tube 686 and the reinforcing sleeve 688, the reinforcing sleeve is desirably shrink tubing fit tightly around the inner tube, and a smooth nose portion 712 is provided at its distal end.

The tip tubing 708 is a 5-lumen construction seen in cross-section in FIG. 16E, with four smaller lumens 714 arranged in an arc on one side, and a larger guidewire lumen 716 on the other side. FIG. 16D illustrates four short longitudinal slots 718 skived in the surface of the tip tubing 708 to a depth that communicates with four smaller lumens 714. In one specific embodiment, the distance A between the proximal end of the tip tubing 708 and the beginning of the slots 718 is approximately 0.075 inches, while the length B of the slots 718 is between about 0.02-0.05 inches. As seen in FIG. 16E, the slots 718 are arranged in an arc around the tip tubing 708 that is less than 180 degrees.

FIGS. 17A and 17B illustrate the clot removal components added to the distal end of the inner tube of the embolectomy catheter 600. In FIG. 17A, the tip tubing 708 has been shortened to a length C of no less than 0.23 inches, and the distal end is provided with a shallow taper 720 resulting in a distal tip diameter $d_{tt}$ of about 0.019 inches. A marker band 720 has been affixed around the tip tubing 708 at a distance D of about 0.02-0.06 inches from the distal end of the slots 718, and at the beginning of the taper 720. The marker band 720 is firmly affixed in this location, such as by adhesive.

FIG. 17B shows a plurality of helical clot removal wires 724 affixed at their distal ends 726 into the slots 718. In a preferred embodiment, the clot removal wires 724 are made of a super-elastic alloy, such as Nitinol, and are bonded within the smaller lumens 714 and slots 718 using a suitable adhesive. A fastener sleeve 728 may be provided to help secure the fixed ends 726 of the wires 724, and to provide a smoother outer surface at the junction.

The clot removal wires 724 extend helically in the proximal direction and each wraps around the distal segment 690 of the reinforced inner tube 680. In a preferred embodiment, a distal wire pair 730 terminates at distal free ends 732, while a proximal wire pair 734 terminates at proximal free ends 736. The free ends 732 and 736 are separated by a sliding marker band 738. The free ends 732 and 736 and sliding marker band 738 are free to slide over the distal segment 690.

FIG. 18A is an elevational view of an unfinished tapered tip 740 that in FIG. 18B has been added to the assembly of FIG. 17B. The unfinished tapered tip 740 has a length $L_{tu}$ of no less than 0.30 inches, and an inner diameter $d_t$ on its large end of about 0.04 inches. The small end inner diameter tapers down to less than the diameter $d_{tt}$ (FIG. 17A), and thus the unfinished tapered tip 740 closely fits about the taper 720, as seen in FIG. 18B. The excess length of the unfinished tapered tip 740 is trimmed at the distal end of the taper 720 so that a final tip 742 is formed. The tip 742 includes a proximal mouth 743.

FIG. 18C illustrates the final assembly of the outer tube distal sheath 676 surrounding the distal end of the inner tube, with the helical clot removal wires 724 shown in their stretched configurations 724'. The distal end 670 of the outer tube distal sheath 676 fits within the mouth 743 of the tapered tip 742 to the extent of an overlap E of approximately 0.02-0.06 inches. As will be explained further below, the distal sheath 676 is not bonded within the tapered tip 742, but is permitted to slide with respect thereto.

FIG. 18C also illustrates the outer tube marker band 744 provided on the distal sheath 676, and a plurality of infusion ports 746 formed along the side wall of the inner tube distal segment 690. As mentioned previously, the outer tube of the catheter 600 slides with respect to the inner tube, and thus the marker band 744 slides with respect to the fixed marker band 722. The infusion ports 746 can be used for injecting contrast media, medications, or fluids designed to dissolve clots. The various uses of the embolectomy catheter 600 of the present invention will be more fully described below.

FIG. 19A is very similar to FIG. 18C, but illustrates the middle segment 674 of the outer tube 650 joined to the distal sheath 676 at the junction 677. In addition, the various components are shown in cross-section so that the infusion ports 746 can be seen formed in the side wall of the inner tube distal segment 690 opposite from the side wall seen in FIG. 18C. The number and spacing of the infusion ports 746 can be varied, as will be explained below with respect to an embodiment shown in FIG. 22.

Exemplary Clot Removal Device

Actuation of the clot removal feature of the embolectomy catheter 600 can be seen most clearly by comparison between FIGS. 19A and 19B. Specifically, the clot removal wires 724' are shown in their stretched and radially contracted configurations in FIG. 19A, and in their relaxed and radially expanded configuration in FIG. 19B, forming an expanded wire nest 750. This transformation is caused by proximal displacement of the outer tube, as indicated by the arrow 752. The clot removal wires 724 normally assume the expanded configuration seen in FIG. 19B if they remain unconstrained, but are held in the stretched configuration 724' by the presence of the surrounding distal sheath 676. Sliding the distal sheath 676 in a proximal direction 752 releases the wires 724, which tend to radially expand, pulling their free ends 732 and 736 in a distal direction. Because the pairs of wires 724 are wrapped around the distal segment 690 on both sides of the sliding marker band 738, the sliding marker band also is pulled distally. The relative spacing between the fixed marker band 722 and sliding marker band 738 provides an indication to the operator about the configuration of the clot removal wires 724.

The outer diameter of the distal end of the embolectomy catheter 600 is extremely small for insertion within very small vessels of the brain, for example. In one particular embodiments, the embolectomy catheter 600 has an outer diameter of about 3 French (Fr) (1 mm).

The expanded wire nest 750 has a diameter that is sized to closely fit within the affected vessel in which the clot has formed or lodged. That is, the wires 724 preferably contact and are slightly outwardly biased against the inner luminal surface of the vessel. The luminal diameter of the target vessels of the present embolectomy catheter 600 are preferably within the range of about 2.5-4.0 mm (0.090-0.110 in), and thus the diameter of the expanded wire nest 750 is also within the range of about 2.5-4.0 mm (0.090-0.110 in). Therefore, the expanded wire nest 750 has an outer diameter that is between 2.5 and 4.0 times the diameter of the distal end of an exemplary 3 Fr catheter 600.

Each of the wires 724 may have a variety of cross-sections, but preferably are circular in cross-section having a diameter of about 0.002 inches. As mentioned above, a preferred material is a super-elastic alloy, such as Nitinol, and the wires 724 are desirably heat set into the nest shape 750 shown in FIG. 19B. The use of an alloy such as Nitinol ensures that the wires 724 remain in their austenitic state, and there is no deformation when they are in their stretched configuration 724' of FIG. 19A. Consequently, each of the wires 724 is spring biased toward its radially expanded configuration, facilitating rapid deployment of the wire nest 750 upon proximal displacement of the outer to distal sheath 676.

In addition, each of the wires 724 has a helical configuration that creates a relatively dense tangle of wires in the nest 750 configuration shown in FIG. 19B. The particular number of wires 724 may be varied, although the smaller the catheter 600 the fewer number of wires that can be accommodated. In a preferred embodiment of a 3 Fr catheter 600, there are between 4 and 6 wires, and more preferably there are 4 as shown.

Wire Pusher Tool

FIGS. 20A and 20B are two views of a clot removal wire pusher 760 having a handle 762 and a pusher portion 764. The pusher portion 764 is relatively long, flat and thin and includes a shaft 766 having a length $L_{sw}$ of about 1.5 inches and pair of side walls 768 on its distal tip forming a shallow U-shape. The shaft 766, on its distal end, has a width $w_{sw}$ and a thickness $t_{sw}$ sufficiently small to fit in the annular space 770 between the inner tube distal segment 690 and the outer tube distal sheath 676 (see FIG. 19A). The wire pusher 760 is thus used to push the free ends 730 and 736 of the clot removal wires 724, and sliding marker band 738, in a proximal direction within the aforementioned annular space 770. In addition, the wire pusher shaft 766 is sufficiently thin and flexible, having a thickness $t_{wp}$, that permits the tool to flex outward at the distal tip 742. While the wire pusher 760 holds the clot removal wires 724 in their stretched configuration, the outer tube distal sheath 676 is advanced in a distal direction into close proximity with the distal tip 742. At the point at which the distal sheath 676 has sufficiently advanced to maintain the clot removal wires 724' in their stretched configuration, the shaft 766 of the wire pusher 760 can be retracted from within the annular space 770. The distal sheath 676 is then displaced distally within the distal tip 742 to create the overlap region E seen in FIG. 18C. In an exemplary embodiment, the shaft 766 has a thickness $t_{wp}$ of about 0.003 inches, and the side walls 768 have a thickness $t_{sw}$ of about 0.012 inches and a width $w_{sw}$ of about 0.036 inches.

Operation of the Preferred Embolectomy Catheter

In operation of the embolectomy catheter 600, the guidewire 604 is first inserted into the catheter 600 and advanced so as to project from the distal end 611. The assembly of the catheter 600 and guidewire 604 is then advanced through a target vessel and through a clot that is previously been located using well-known visualization means. The leading guidewire 604 and tapered distal tip 742 facilitate passage of the catheter 600 through the clot. Additionally, the distal end of the outertube distal sheath 676 is prevented from catching on the clot as the catheter body passes therethrough by virtue of its insertion within the mouth 743 of the tapered tip 742. After a suitable length of the catheter 600 is advanced past the clot, as can be verified by the location of the fixed marker band 722, the clot removal nest 750 is deployed.

As mentioned previously, displacement of the sliding infusion port 630 in a proximal direction relative to the handle body 612 (see FIG. 11A) causes deployment of the clot removal nest 750. That is, as best seen in FIGS. 12 and 12A, the sliding infusion port 630 is fixed axially with respect to the outer tube 650. As the operator displaces the sliding infusion port 630 along the channel 618 in a proximal direction, the outer tube 650 is pulled with respect to the reinforced inner tube 680. An infusion drip through the infusion port 640 hydrates and lubricates hydrophilic coatings provided on the inner surface of the outer tube 650, and the outer surface of the reinforced inner tube 680. More particularly, a lubricious coating is provided on these opposing surfaces. This lubrication helps the outer tube 650 slide proximally over the reinforced inner tube 680.

Displacement of the outer tube 650 over the reinforced inner tube 680 results in the transformation from FIG. 19A to FIG. 19B. That is, the outer tube distal sheath 676 slides in the direction 752 to release the wires 724 to form the expanded wire nest 750. Again, displacement of the sliding marker band 738 toward the fixed marker band 722 indicates to the operator that deployment of the wire nest 750 has occurred. Desirably, the outer tube distal sheath 676 that constrains the clot removal device 724 in its collapsed configuration has a substantially lower column strength than that portion of the reinforced inner tube 680 about which the clot removal device is mounted. This helps increase flexibility of the catheter 600 at the distal end, while still ensuring adequate column strength to enable the telescoping deployment. The operator may, if desired, tighten the bolt 646 to maintain the relative positions of the inner and outer tubes so that the clot removal device 724 is held in its deployed configuration.

At this point, the entire catheter 600 is retracted in a proximal direction over or with the guidewire 604 to cause the expanded wire nest 750 to become entangled within the clot. Rotation of the catheter 600, or rotation of the reinforced inner tube 680 alone, helps the wire nest 750 to entangle and entrap the clot. This portion of the procedure is similar to that shown in FIGS. 8D-8F in conjunction with an earlier-described embodiment of the present invention.

Operation of Alternative Embolectomy Catheters of the Present Invention

FIGS. 21-24 illustrate various clot removal techniques that can be practiced with one or more of the specific catheter embodiments described herein. Although certain techniques, such as balloon occlusion and aspiration, are well-known in the art, the present inventors believe that the over-the-wire catheters of the present invention permit novel combinations that provide significant advantages over the prior art. That is, passing a guidewire first through the clot provides a vehicle over which a variety of clot removal devices can be passed to the downstream side of the clot. Access to both sides of clot provides an operator with flexibility previously unknown. Although some devices of the prior art show catheters passing through the clot to, for example, expand a balloon on the downstream side of the clot, none of these devices are suitable for removing clots in extremely small vessels. Consequently, the present invention provides devices and methods for small vessel clot removal that are a significant advance in the treatment of ischemic stroke, for example.

Figure 21A:
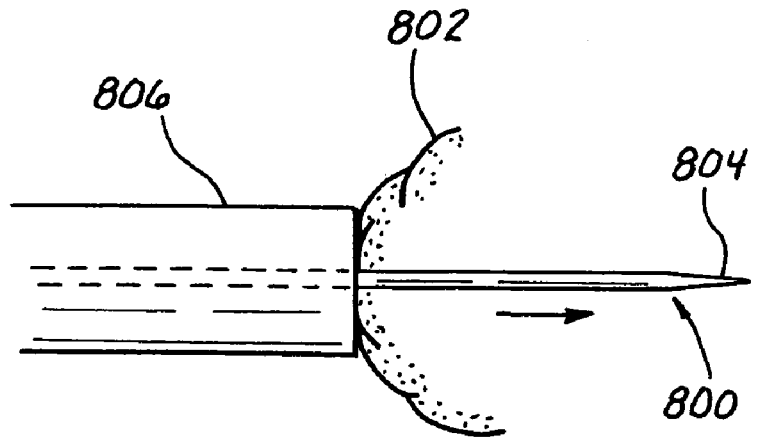
FIG. 21A illustrates a guidewire of the present invention passing through a clot.
Figure 21B:
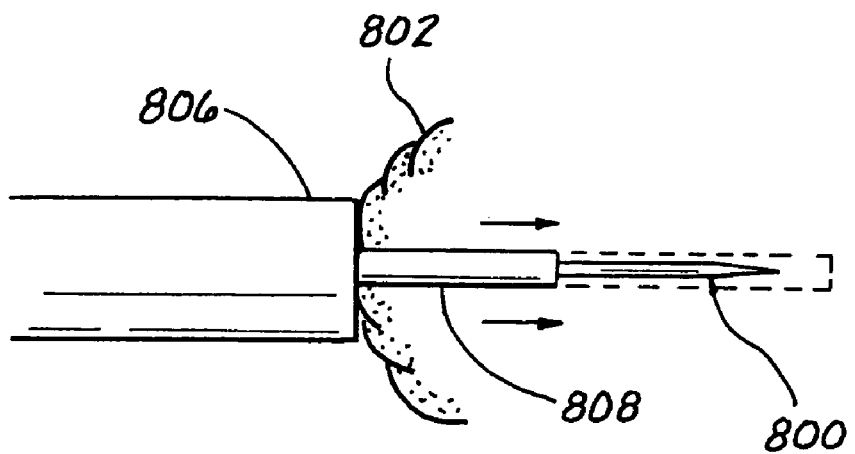
FIG. 21B illustrates a catheter of the present invention advancing over the guidewire of FIG. 21A that has previously been partially or fully advanced through the clot.

FIGS. 21A and 21B illustrate the basic advance of the present invention in passing a guidewire 800 through a clot 802. The guidewire 800 is shown having a tapered tip 804, and may be especially designed to penetrate a clot 802 as, for example, with the provision of a sharpened tip. An outer catheter shaft 806 is shown advanced into close proximity with the clot 802, which location can be easily reached with the use of marker bands and radiographic visualization.

FIG. 21B illustrates the advancement of an inner catheter shaft 808 over the guidewire 800. One significant advantage of first passing the guidewire 800 through the clot 802 is that a first inner catheter shaft 808 can be introduced, utilized, and then removed, and a second catheter shaft can be introduced. In this manner, a variety of treatments and/or devices can be applied to remove the clot 802 utilizing a single guidewire 800 which remains in place. This saves time and reduces trauma to the patient.

Figure 22:
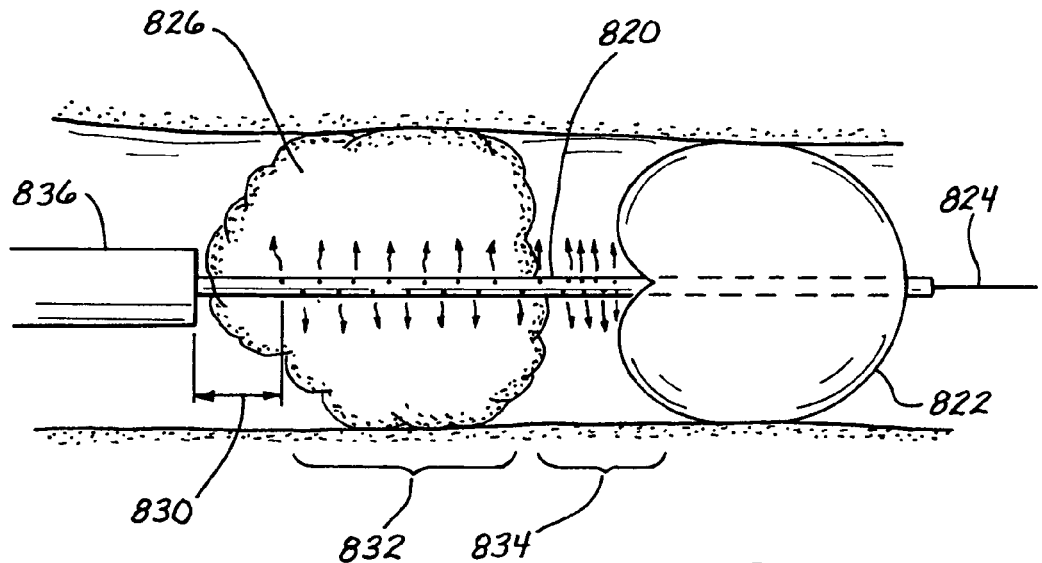
FIG. 22 is a cross-section through a vessel showing the operation of an infusion catheter of the present invention for clot removal.

FIG. 22 is a cross-section through a vessel showing an infusion catheter 820 having an expanded balloon 822 on its distal end after having been advanced over a guidewire 824 and through a clot 826. As mentioned above with respect to the infusion ports 746 seen in FIGS. 18 and 19, the infusion catheter 820 can have variable infusion port spacing along its length. More specifically, the infusion catheter 820 includes a proximal region 830 with few or no infusion ports, a middle region 832 embedded in the clot 826 with infusion ports that are more concentrated in the center, and a distal region 834 with a large concentration of infusion ports. The relative flow of fluid through these infusion ports is illustrated schematically.

In a preferred embodiment, fluid suitable for breaking up the clot 826 is introduced through the ports of the infusion catheter 820. Because of the balloon 822, the fluid stays in the region of clot 826 for more effective clot dissolution. In addition, injecting dissolution fluid in the middle of the clot 826 facilitates its internal breakup. Furthermore, the larger flow of fluid from the distal region 834 helps create a pressure gradient which forces the clot 826 in the proximal direction toward the catheter shaft 836.

Figure 23A:
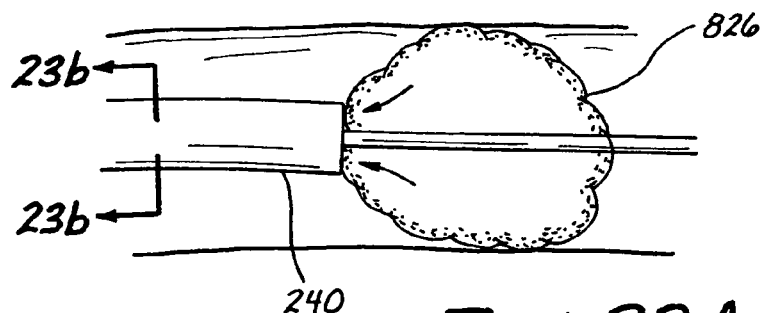
FIG. 23A is a longitudinal cross-section through a vessel showing the operation of an aspirating catheter of the present invention for clot removal.
Figure 23B:
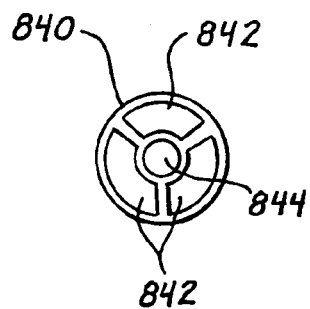
FIG. 23B is a transverse cross-section through the aspirating catheter of FIG. 23A.

FIGS. 23A and 23B illustrate a catheter shaft 840 that has a multiple lumen cross-section with a plurality of aspiration ports 842 in addition to the central guidewire port 844. The catheter shaft 840 can be used in conjunction with the arrangement shown in FIG. 22 to aspirate the clot 826 as it breaks up.

Figure 24B:
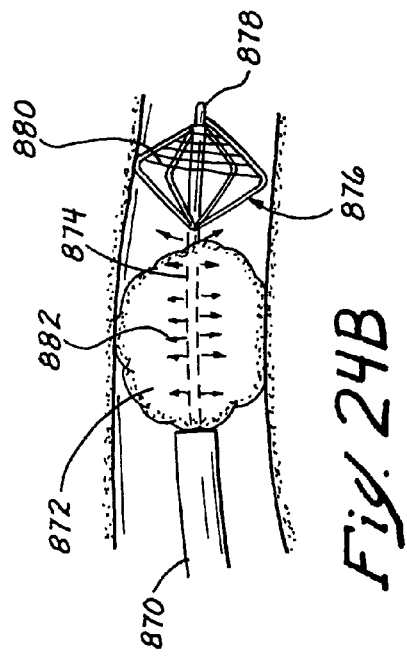
FIGS. 24B-24D are cross-sections through a vessel showing the operation of an infusion catheter of the present invention in combination with various distal clot capture devices.
Figure 24D:
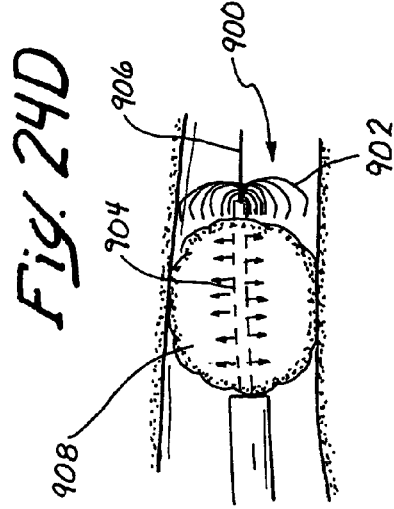
Figure 24A:
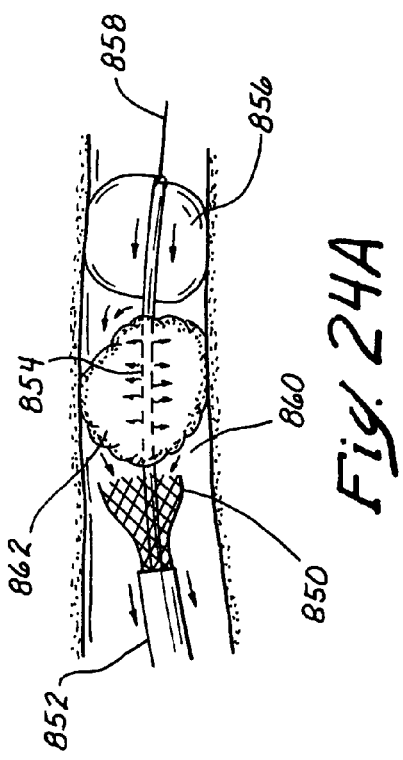
FIG. 24A is a cross-section through a vessel showing the operation of an infusion catheter of the present invention in combination with an occlusion balloon and a proximal clot capture device.

FIG. 24A illustrates a clot removal device similar to that shown in FIG. 22, with the addition of an expandable receptacle 850 shown extended from the distal end of a retractable catheter sheath 852. The infusion catheter 854 and balloon 856 have been advanced over a guidewire 858. The use of suction, as indicated by the arrows 860, may be combined with the expandable receptacle 852 to capture the dissolving clot 862 as it migrates in a proximal direction.

FIG. 24B shows an outer catheter shaft 870 adjacent a clot 872 with an infusion catheter 874 and expandable clot trap 876 advanced over a guidewire 878 through the clot. The expandable clot trap 876 may be any of the embodiments described previously, and is shown as individual spring members attached at both ends to the infusion catheter 874. A webbing 880 may also be provided to help capture small particles of dissolving clot material. Infusate 882 from the catheter 874 is also shown to facilitate clot breakup. Again, aspiration may be combined with this arrangement.

Figure 24C:
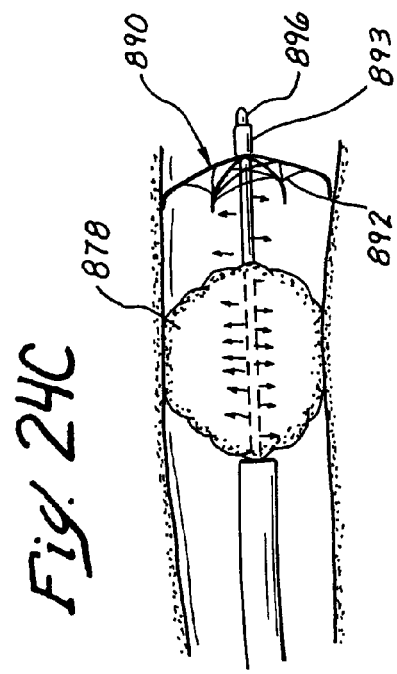

FIG. 24C is similar to the configuration of FIG. 24B but includes an expandable clot trap 890 comprising a plurality of umbrella-like struts with a webbing 892 therebetween. A collar 893 may be provided for collapsing the clot trap 890. Again, the infusion catheter 894 and clot trap 890 have been advanced over a guidewire 896 that had previously penetrated through the clot 898.

Finally, FIG. 24D is an arrangement similar to that shown in FIGS. 24B and 24C, but includes a clot removal trap 900 made up of a plurality of curvilinear spring wires 902 projecting from the end of the infusion catheter 904. The spring wires 902 may pass through individual lumens formed within the infusion catheter 904, and preferably have rounded tips to prevent vessel perforation. Once again, a guidewire 906 is first advanced through the clot 908.

Infusion Guidewire

In addition to the advantages provided by a guidewire that permits sustained access to downstream side of clot, the present invention contemplates the use of a special type of guidewire that can be used to infuse fluid. Although small infusion catheters are known in the art, the present invention is believed to be the first device that can infuse fluid on the downstream side of a clot in extremely small vessels, such as the vessels of the brain. This feature, in conjunction with the previously described advantages of locating a guidewire through a clot as a vehicle for clot removal catheters is a significant improvement on the prior art.

A specific example of an infusion guidewire 920 of the present invention is schematically shown in FIGS. 25A and 25B. The infusion guidewire 920 comprises an inner wire member 922 and an outer sleeve member 924. The guidewire 920 is shown inserted through a micro-catheter 926 having a proximal region with a length $L_1$, a tapered middle region with a length $L_2$, and a distal region with a length $L_3$. These lengths may be for example: $L_1$=100 cm, $L_2$=20 cm, and $L_3$=20 cm; with the axial lengths shown schematically.

The wire member 922, has an outer diameter of about 0.007 inches. The sleeve member 924, in turn, has an inner diameter of a slightly greater size, preferably about 0.008 inches. The outer diameter of the sleeve member 924 is preferably about 0.010 inches. The inner diameter of the distal region $L_3$ of the micro-catheter 926 closely fits around the sleeve member 924, however, in the proximal region $L_1$, an annular space 928 is creating between the sleeve member 924 and the inner lumen 930 of the micro-catheter 926.

The wire member 922, by virtue of its slightly smaller dimension, may be displaced longitudinally within the sleeve member 924, as indicated by the arrow 932 of FIG. 25B. A plurality of side ports 934 are provided in the sleeve member 924 in the middle region $L_2$ of the micro-catheter 926. Therefore, after the wire member 922 has been retracted into the position shown into 25B, fluid infused through the annular space 928 can pass through the side ports 934 into a lumen 936 of the sleeve member 924, and from there out of its distal tip 938.

Figure 26A:
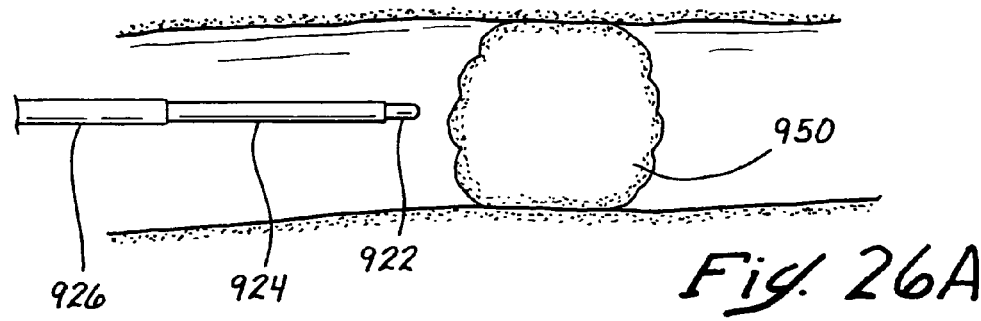
FIGS. 26A-26D are longitudinal cross-sections through a vessel showing the use of an infusion guidewire of the present invention.
Figure 26B:
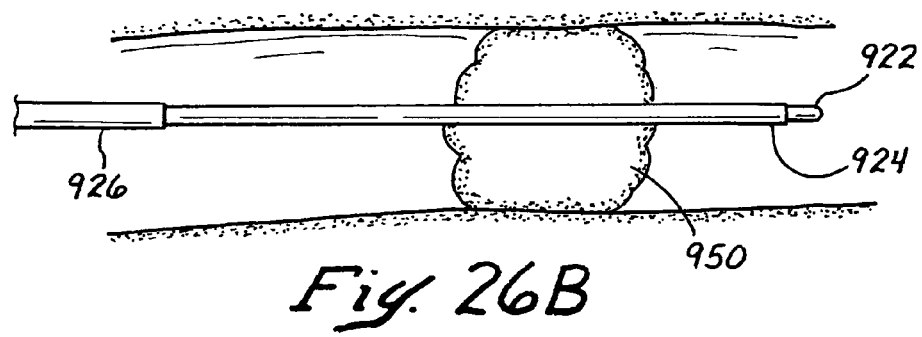
Figure 26C:
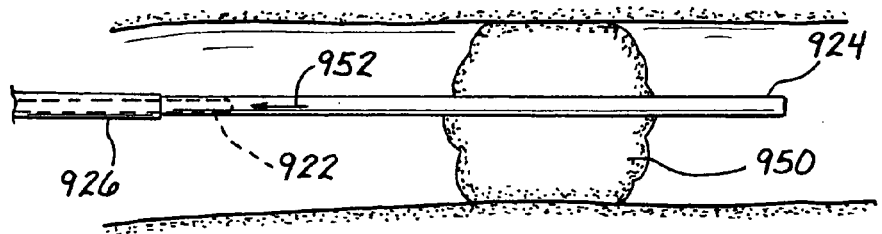

In use, the infusion guidewire of the present invention is advanced through blood vessel toward a clot 950, as seen in FIG. 26A. The wire member 922 and sleeve member 924 may be advanced independently, or into proximity with a clot 950 within the micro-catheter 926. FIG. 26B illustrates the infusion guidewire comprising the wire member 922 and sleeve member 924 having penetrated the clot 950 to a downstream side. Subsequently, as seen in FIG. 26C, the wire member 922 is withdrawn as indicated by the arrow 952, leaving the sleeve member 924 in place on the downstream side of clot 950. Fluid can then be infused through the sleeve member 924, as indicated at 954 in FIG. 26D. Such fluid can be, for example, medications, clot dissolution chemicals, or contrast media.

Figure 26D:
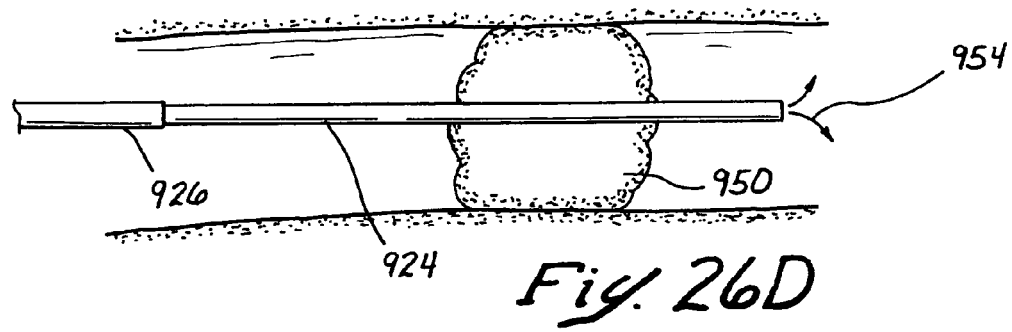

The advantages of being able to infuse fluid on the downstream side of a clot have been explained previously, but one particular advantage is the ability to inject contrast media to better visualize the size and position of the clot 950. Thus for example contrast media may be injected at 954 as seen in FIG. 26D in anticipation of use of one of the clot removal devices of the present invention.

Figure 27A:
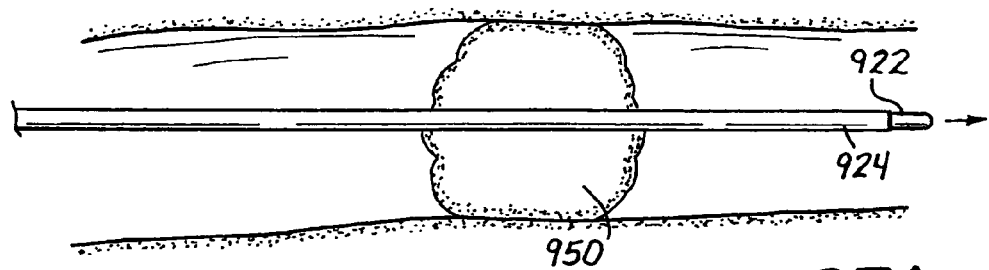
FIGS. 27A-27D are longitudinal cross-sections through a vessel showing the deployment of a clot removal device over the infusion guidewire of the present invention.
Figure 27B:
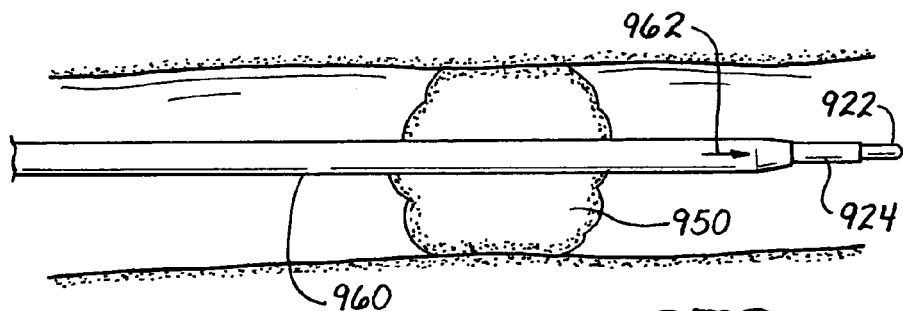
Figure 27C:
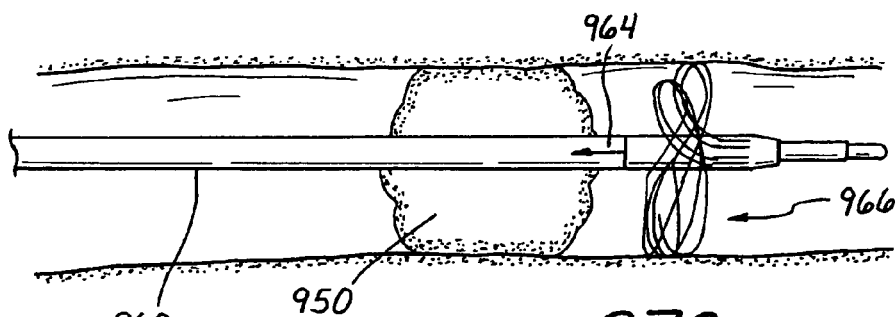
Figure 27D:
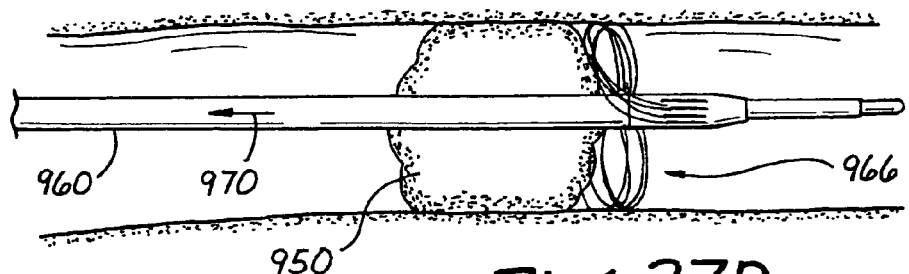

Prior to introduction of an embolectomy catheter of the present invention, the wire member 922 is desirably reinserted within the sleeve member 924 to provide suitable rigidity, as seen in FIG. 27A. Thereafter, as in FIG. 27B, an embolectomy catheter 960 is advanced along the infusion guidewire and through the clot 950, as indicated by the arrow 962. Subsequently, the telescoping element of the embolectomy catheter 960 is retracted, as indicated at 964 in FIG. 27c, to release a clot removal device 966, such as the helical wires described above with respect to FIGS. 18 and 19. Of course, any of the embolectomy catheters of the present invention can be substituted. Finally, as seen in FIG. 27d, the embolectomy catheter 960 is retracted as indicated the arrow 970 to cause the clot removal device 966 to become entangled with and remove the clot 950.

It is to be appreciated that the invention has been described herein with reference to certain exemplary embodiments only, and no effort has been made to exhaustively describe each an every possible embodiment of the invention. For example, the specific dimensions given herein are not to be considered limiting. Indeed, as those skilled in the art will appreciate, various additions, deletions, modifications and/or alterations may be made to he above described embodiments without departing from the spirit and scope of the invention. It is intended that all such additions, deletions, alterations and modifications be included within the scope of the following claims.

What is claimed is:

1. An embolectomy catheter system for removing a blood clot or other embolus from a location within the vasculature of a human or animal subject, the catheter comprising:
   a guidewire;
   an embolectomy catheter that is advanceable over said guidewire, said embolectomy catheter comprising:
   an elongate flexible catheter body having a proximal end, a distal end, an inner tube, and an outer tube terminating proximal to a distal end of the catheter body;
   an embolus removal apparatus disposed on the inner tube, the embolus removal apparatus being initially disposed in a collapsed configuration and constrained in said collapsed configuration by a portion of the outer tube; and
   a distal tip of the catheter body being located on the inner tube and adapted to pass through a blood clot or other embolus to be removed;
   wherein the outer tube is configured to be axially retractable to remove the constraint on the embolus removal apparatus and whereby the embolus removal apparatus is configured to automatically expand from said collapsed configuration to a deployed configuration upon said axial retraction of said outer tube without requiring axial movement or rotation of the guidewire;
   said embolus removal apparatus comprising a plurality of resilient members having proximal ends configured to freely slide over said inner tube and distal ends fixed to said inner tube and mid-portions that are configured to extend laterally away from the catheter body when the proximal ends slide over said inner tube as said embolus removal apparatus achieves its deployed configuration, thereby allowing embolic material to become entangled in said resilient members, said resilient members being wrapped around said inner tube in a helical manner when in said collapsed configuration.

2. A system according to claim 1, wherein the outer tube extends distally within a proximal mouth of the distal tip prior to being retracted.

3. A system according to claim 1 wherein a lumen through which the guidewire may pass extends through the inner tube and through the embolus removal device.

4. A system according to claim 1 further comprising a plurality of infusion ports located near said embolus removal apparatus.

5. A system according to claim 1 wherein the embolus removal apparatus expands from its collapsed configuration to its deployed configuration without requiring rotation of any portion of the embolectomy catheter or guidewire.

6. A system according to claim 1 wherein said proximal ends of said resilient members are separated by a marker band that is slidably mounted on said inner tube.

7. A system according to claim 1 wherein said resilient members are biased to have an expanded configuration.

8. A system according to claim 1 wherein said resilient members form an expanded wire nest when said embolus removal apparatus is in said deployed position.

* * * * *